United States Patent
Hobbs, Jr.

(10) Patent No.: US 6,703,420 B1
(45) Date of Patent: Mar. 9, 2004

(54) AMINO-THIO-ACRYLONITRILES AS MEK INHIBITORS

(75) Inventor: Frank Worden Hobbs, Jr., Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/527,335

(22) Filed: Mar. 17, 2000

Related U.S. Application Data

(60) Provisional application No. 60/125,330, filed on Mar. 19, 1999.

(51) Int. Cl.[7] .................... A61K 31/275; C07C 255/00
(52) U.S. Cl. ....................... 514/523; 558/390
(58) Field of Search .................... 564/305; 514/646, 514/277, 523; 546/330; 558/390

(56) References Cited

FOREIGN PATENT DOCUMENTS

WO 9837881 9/1998

OTHER PUBLICATIONS

Morel, et. al., Synthesis of Thiomidates by Insertion of Tert–Butylisocyanide into the C–S Bond of Activated Sulfides. Rearrangement of Thiomidates By 1,3 C to N Migration of An alkoxycarbonyl Group, 1984.*

Morel et. al., "C–(Methoxycarbonyl)ketene N–imidoylimine synthesis rearrangement into methyl 4,6–diazahepta–2,4,6–trienoates. Cycloaddition reactions with isocyanides: preparation of imidazolines", J. Org. Chem., 50(6), 771–8, pp. 771–778.*

Favata et al., Identification of a Novel Inhibitor of Mitogen–activated Protein Kinase Kinase, J. Biol. Chem. (1998) 29, 18623–18632.

Duncia et al., MEK Inhibitors, The Chemistry and Biological Activity of U0126, Its Analogs, and Cyclization Products, Bioorganic & Medicinal Chemistry Letters (1998) 2839–2844.

* cited by examiner

Primary Examiner—Alan L. Rotman
Assistant Examiner—Binta Robinson
(74) Attorney, Agent, or Firm—Mary K. VanAtler

(57) ABSTRACT

This invention relates generally to amino-thio-acrylonitriles of formula Ia or Ib:

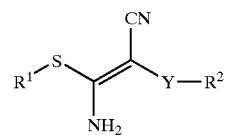

Ia

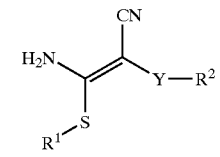

Ib as MEK inhibitors, pharmaceutical compositions containing the same, and methods of using the same as for treatment and prevention of inflammatory disorders or as an anticancer radiosensitizing agent.

11 Claims, No Drawings

AMINO-THIO-ACRYLONITRILES AS MEK INHIBITORS

This application claims benefit of Ser. No. 60/125,330 filed Mar. 14, 1999.

FIELD OF THE INVENTION

This invention relates generally to amino-thio-acrylonitriles as MEK inhibitors, pharmaceutical compositions containing the same, and methods of using the same as for treatment and prevention of inflammatory disorders, cancer or other proliferative diseases or as a radiosensitizing agents against cancer or other proliferative disorders.

BACKGROUND OF THE INVENTION

The mitogen activated protein kinase (MAPK) signaling pathways are involved in cellular events such as growth, differentiation and stress responses (*J. Biol. Chem.* (1993) 268, 14553–14556). Four parallel pathways have been identified to date ERK1/ERK2, JNK, p38 and ERK5. These pathways are linear kinase cascades in that MAPKKK phosphorylates and activates MAPKK that phosphorylates and activates MAPK. To date, there are 7 MAPKK homologs (MEK1, MEK2, MKK3, MKK4/SEK, MEK5, MKK6, and MKK7) and 4 MAPK families (ERK1/2, JNK, p38, and ERK5). The MAPKK family members are unique in that they are dual-specific kinases, phosphorylating MAPKs on threonine and tyrosine. Activation of these pathways regulates the activity of a number of substrates through phosphorylation. These substrates include transcription factors such as TCF, c-myc, ATF2 and the AP-1 components, fos and Jun; the cell surface components EGF-R; cytosolic components including PHAS-I, $p90^{rsk}$, $cPLA_2$ and c-Raf-1; and the cytoskeleton components such as tau and MAP2.

The prototypical mitogen activated protein kinase cascade is reflected by the ERK pathway (*Biochem J.* (1995) 309, 361–375). The ERK pathway is activated primarily in response to ligation of receptor tyrosine kinases (RTKs) (*FEBS Lett.* (1993) 334, 189–192). Signal propagation from the RTKs occurs down the Ras pathway through sequential phosphorylation of Raf, MEK and ERK. This pathway has not been typically viewed of as an important contributor to the inflammatory response, but rather involved in growth and differentiation processes. This view stems from the profile of typical activators of this pathway, which include growth factors (PDGF, NGF, EGF), mitogens (phorbol esters), and polypeptide hormones (insulin, IGF-1). Evidence for ERK pathway involvement in inflammatory and immune responses has, however, gained some support in recent years (*Proc. Natl. Acad. Sci. USA.* (1995) 92, 1614–1618; *J. Immunol.* (1995) 155, 1525–1533; and *J. Biol. Chem.* (1995) 270, 27391–27394). Cytokines such as TNFa and IL-1b, the bacterial cell wall mitogen, LPS, and chemotactic factors such as fMLP, C5a, and IL-8 all activate the ERK pathway. In addition, the ERK pathway is activated as a result of T cell receptor ligation with antigen or agents such as PMA/ionomycin or anti-CD3 antibody, which mimic TCR ligation in T cells (*Proc. Natl. Acad. Sci. USA* (1995) 92, 7686–7689). These findings indicate that inhibitors of the ERK pathway should function as anti-inflammatory and immune suppressive agents.

Small molecule inhibitors of the Raf/MEK/ERK pathway have been identified. A series of benzoquinones has been disclosed by Parke-Davis, which is exemplified by PD 098059 that inhibits MEK activity (*J. Biol. Chem.* (1995) 46, 27498–27494). Recently, we identified a MEK inhibitor, U0126 (*J. Biol. Chem.* (1998) 29, 18623–18632). Comparative kinetic analysis showed that U0126 and PD 098059 were non-competitive inhibitors of activated MEK (*J. Biol. Chem.* (1998) 29, 18623–18632). These MEK inhibitors have been used to investigate the role of the ERK activation cascade in a wide variety of systems including inflammation, immune suppression and cancer. For example, PD 098059 blocks thymidine incorporation into DNA in PDGF-stimulated Swiss 3T3 cells (*J. Biol. Chem.* (1995) 46, 27498–27494). PD 098059 also prevents PDGF-BB-dependent SMC (Smooth Muscle Cell) chemotaxis at concentrations which inhibit ERK activation (*Hypertension* (1997) 29, 334–339). Similarly, U0126 prevents PDGF-dependent growth of serum starved SMC. We have also shown that U0126 blocks keratinocyte proliferation in response to a pituitary growth factor extract, which consists primarily of FGF. These data coupled with those obtained with PD 098059 above indicate that MEK activity is essential for growth factor-stimulated proliferation.

The role of the MEK/ERK pathway in inflammation and immune suppression has been examined in a number of systems, including models of T cell activation. The T cell antigen receptor (TCR) is a non-RTK receptor whose intracellular signaling pathways have been elucidated (*Proc. Natl. Acad. Sci. USA* (1995) 92, 7686–7689). DeSilva et al. have generated a great deal of information with U0126 in T cell systems (*J. Immunol.* (1998) 160, 4175–4181). Their data showed that U0126 prevents ERK activation in T cells in response to PMA/ionomycin, Con A stimulation, and antigen in the presence of costimulation. In addition, T cell activation and proliferation in response TCR engagement is blocked by U0126 as is IL-2 synthesis. These results indicate that MEK inhibition does not result in a general antiproliferative effect in this IL-2-driven system, but selectively blocks components of the signaling cascades initiated by T cell receptor engagement.

PD 098059 has also been shown to inhibit T cell proliferation in response to anti-CD3 antibody, which is reversed by IL-2 (*J. Immunol.* (1998) 160, 2579–2589.). PD 098059 also blocked IL-2 production by T cells stimulated with anti-CD3 antibody in combination with either anti-CD28 or PMA. In addition, the MEK inhibitor blocked TNFa, IL-3 GM-CSF, IFN-g, IL-6 and IL-10 production. In contrast, PD 098059 enhanced production of IL-4, IL-5 and IL-13 in similarly stimulated T cell cultures. These differential T cells effects with MEK inhibition suggest that therapeutic manipulations may be possible.

Neutrophils show ERK activation in response to the agonists N-formyl peptide (fMLP), IL-8, C5a and $LTB_4$, which is blocked by PD 098059 (*Biochem. Biophy. Res. Commun.* (1997) 232, 474–477). Additionally, PD 098059 blocks neutrophil chemotaxis in response to all agents, but does not alter superoxide anion production. However, fMLP-stimulated superoxide generation was inhibited by PD098059 in HL-60 cells (*J. Immunol.* (1997) 159, 5070–5078), suggesting that this effect may be cell-type specific. U0126 blocks ERK activation in fMLP- and $LTB_4$-stimulated neutrophils, but does not impair NADPH-oxidase activity or bacterial cell killing. U0126 at 10 mM blunts up regulation of b2 integrin on the cell surface by 50% and blocks chemotaxis through a fibrin gel >80% in response to IL-8 and $LTB_4$. Thus, neutrophil mobility is affected by MEK inhibition although the acute functional responses of the cell remain intact.

Eicosanoids are key mediators of the inflammatory response. The proximal event leading to prostaglandin and leukotriene biosynthesis is arachidonic acid release from membrane stores, which is mediated largely through the action of cytosolic phospholipase $A_2$ (cPLA$_2$). Activation of cPLA$_2$ requires $Ca^{2+}$ along with phosphorylation on a consensus MAP kinase site, Ser505, which increases catalytic efficiency of the enzyme (*J. Biol. Chem.* (1997) 272, 16709–16712). In neutrophils, mast cells, or endothelial cells, PD 098059 blocks arachidonic acid release in response to opsonized zymosan, aggregation of the high affinity IgG receptor, or thrombin, respectively. Such data support a role for ERK as the mediator of cPLA$_2$ activation through phosphorylation (*FEBS Lett.* (1996) 388, 180–184. *Biochem J.* (1997) 326, 867–876 and *J. Biol. Chem.* (1997) 272, 13397–13402). Similarly, U0126 is able to block arachidonic acid release along with prostaglandin and leukotriene synthesis in keratinocytes stimulated with a variety of agents. Thus, the effector target, cPLA$_2$, is sensitive to MEK inhibition in a variety of cell types.

MEK inhibitors also seem to affect eicosanoid production through means other than inhibition of arachidonic acid release. PD 098059 partially blocked LPS-induced Cox-2 expression in RAW 264.7 cells, indicating ERK activation alone may not be sufficient to induce expression of this key enzyme mediating inflammatory prostanoid production (*Biochem J.* (1998) 330, 1107–1114). Similarly, U0126 inhibits Cox-2 induction in TPA-stimulated fibroblasts, although it does not impede serum induction of the Cox-2 transcript. PD 098059 also inhibits Cox-2 induction in lysophosphatidic acid (LPA)-stimulated rat mesangial cells, which further supports a role for ERK activation in production of prostaglandins (*Biochem J.* (1998) 330, 1107–1114). Finally, 5-lipoxygenase translocation from the cytosol to the nuclear membrane along with its activation as measured by 5-HETE production can be inhibited by PD 098059 in HL-60 cells (*Arch. Biochem. Biophys;* (1996) 331, 141–144).

Inflammatory cytokines such as TNFa and IL-1b are critical components of the inflammatory response. Cytokine production in response to cell activation by various stimuli as well as their activation of downstream signaling cascades represent novel targets for therapeutics. Although the primary effect of IL-1b and TNF-a is to up regulate the stress pathways (*Nature* (1994) 372, 729–746), published reports (*Proc. Natl. Acad. Sci. USA* (1995) 92, 1614–1618. *J. Immunol.* (1995) 155, 1525–1533. *J. Biol. Chem.* (1995) 270, 27391–27394. *Eur. J.*). Cytokines such as TNFa and IL-1b, the bacterial cell wall mitogen, LPS, and chemotactic factors such as fMLP, C5a, and IL-8 all activate the ERK pathway. In addition, the ERK pathway is activated as a result of T cell receptor ligation with antigen or agents such as PMA/ionomycin or anti-CD3 antibody, which mimic TCR ligation in T cells (*Proc. Natl. Acad. Sci. USA* (1995) 92, 7686–7689) and clearly show that the ERK pathway is also affected. U0126 can block MMP induction by IL-1b and TNF-a in fibroblasts (*J. Biol. Chem.* (1998) 29, 18623–18632), demonstrating that ERK activation is necessary for this proinflammatory function. Similarly, lipopolysaccharide (LPS) treatment of monocytes results in cytokine production that has been shown to be MAP kinase-dependent being blocked by PD 098059 (*J. Immunnol.* (1998) 160, 920–928). Indeed, we have observed similar results in freshly isolated human monocytes and THP-1 cells where LPS-induced cytokine production is inhibitable by U0126 (*J. Immunol.* (1998) 161:5681–5686).

The proximal involvement of RAS in the activation of the ERK pathway suggests that MEK inhibition might show efficacy in models where oncogenic RAS is a determinant in the cancer phenotype. Indeed, PD 098059 (*J. Biol. Chem.* (1995) 46, 27498–27494) as well as U0126 are able to impede the growth of RAS-transformed cells in soft agar even though these compounds show minimal effects on cell growth under normal culture conditions. We have further examined the effects of U0126 on the growth of human tumor cell lines in soft agar. We have shown that U0126 can prevent cell growth in some cells, but not all, suggesting that a MEK inhibitor may be effective in only certain kinds of cancer. In addition, PD 098059 has been shown to reduce urokinase secretion controlled by growth factors such as EGF, TGFa and FGF in an autocrine fashion in the squamous cell carcinoma cell lines UM-SCC-1 and MDA-TV-138 (*Cancer Res.* (1996) 56, 5369–5374). In vitro invasiveness of UM-SCC-1 cells through an extracellular matrix-coated porous filter was blocked by PD 098059 although cellular proliferation rate was not affected. These results indicate that control of the tumor invasive phenotype by MEK inhibition may also be a possibility. The observed effects with PD 098059 and U0126 suggest that MEK inhibition may have potential for efficacy in a number of disease states. Our own data argue strongly for the use of MEK inhibitors in T-cell mediated diseases where immune suppression would be of value. Prevention of organ transplant rejection, graft versus host disease, lupus erythematosus, multiple sclerosis, and rheumatoid arthritis are potential disease targets. Effects in acute and chronic inflammatory conditions are supported by the results in neutrophils and macrophage systems where MEK inhibition blocks cell migration and liberation of proinflammatory cytokines. A use in conditions where neutrophil influx drives tissue destruction such as reperfusion injury in myocardial infarction and stroke as well as inflammatory arthritis may be warranted. Blunting of SMC migration and inhibition of DNA replication would suggest atherosclerosis along with restenosis following angioplasty as disease indications for MEK inhibitors. Skin disease such as psoriasis provides another potential area where MEK inhibitors may prove useful since MEK inhibition prevents skin edema in mice in response to TPA. MEK inhibition also blocks keratinocyte responses to growth factor cocktails, which are known mediators in the psoriatic process.

Finally, the use of a MEK inhibitor in cancer can not be overlooked. Ionizing radiation initiates a process of apoptosis or cell death that is useful in the treatment solid tumors. This process involves a balance between pro-apoptotic and anti-apoptotic signal (*Science* 239, 645–647), which include activation of MAP kinase cascades. Activation of the SAPK pathway delivers a pro-apoptotic signal (*Radiotherapy and Oncology* (1998) 47, 225–232.), whereas activation of the MAPK pathway is anti-apoptotic (*Nature* (1996) 328, 813–816.). Interference with the anti-apoptotic MAPK pathway by dominant negative MEK2 or through direct inhibition of MEK with synthetic inhibitors sensitizes cells to radiation-induced cell death (*J. Biol. Chem.* (1999) 274, 2732–2742; and *Oncogene* (1998) 16, 2787–2796).

WO98/37881 describe MEK inhibitors useful for treating or preventing septic shock. The inhibitors include 2-(2-amino-3-methoxyphenyl)-4-oxo-4H-[1]benzopyran and a compound of the formula:

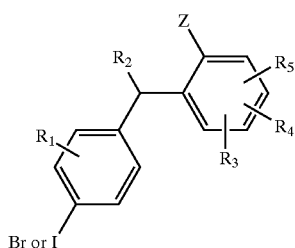

Br or I

The above diphenyl amines are not considered to be part of the presently claimed invention.

Therefore, efficacious and specific MEK inhibitors are needed as potentially valuable therapeutic agents for the treatment of inflammatory disorders, cancer or other proliferative diseases or as a radiosensitizing agents against cancer or other proliferative disorders. It is thus desirable to discover new MEK inhibitors.

SUMMARY OF THE INVENTION

Accordingly, one object of the present invention is to provide novel amino-thio-acrylonitriles which are useful as MEK inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating a disorder involving MEK, comprising: administering to a host in need of such treatment a therapeutically effective amount of at least one of the compounds of the present invention or a pharmaceutically acceptable salt or prodrug form thereof.

It is another object of the present invention to provide a novel method of using the compounds of the present invention as a radiosensitizing agent for the treatment of cancers or proliferative diseases, comprising: administering to a host in need of such treatment a therapeutically effective amount of a compound of the present invention, or a pharmaceutically acceptable prodrug or salt form thereof.

It is another object of the present invention to provide a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

It is another object of the present invention to provide a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

It is another object of the present invention to provide novel amino-thio-acrylonitriles or salts or prodrugs thereof for use in therapy.

It is another object of the present invention to provide the use of novel amino-thio-acrylonitriles or salts or prodrugs thereof for the manufacture of a medicament for the treatment of an inflammatory disease.

It is another object of the present invention to provide the use of novel amino-thio-acrylonitriles or salts or prodrugs thereof for the manufacture of a medicament for the treatment of cancer.

These and other objects, which will become apparent during the following detailed description, have been achieved by the inventors' discovery that compounds of formula Ia or Ib:

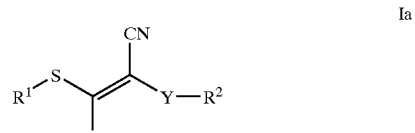

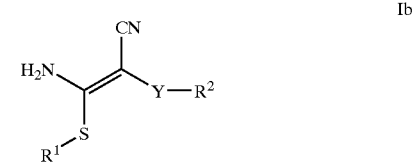

or pharmaceutically acceptable salt or prodrug forms thereof, wherein $R^1$ and $R^2$ are defined below, are effective MEK inhibitors.

DETAILED DESCRIPTION OF PREFERRED EMBODIMENTS

Thus, in a first embodiment, the present invention provides a novel compound of formula Ia or Ib:

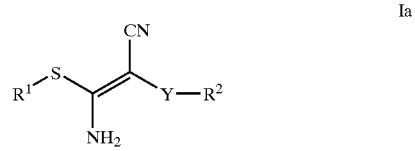

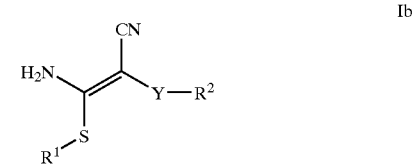

or stereoisomer or pharmaceutically acceptable salt form thereof, wherein;

$R^1$ is phenyl, naphthyl, 2,3-dihydroindol-5-yl or a 5–6 membered heteroaryl ring with 1–4 heteroatoms selected from N, NH, O, and S, and $R^1$ is substituted with 0–2 $R^a$;

$R^a$ is selected from H, Cl, F, Br, I, $C_{1-4}$ alkyl, $C_{1-4}$ alkoxy, OH, $CH_2OH$, $NH_2$, $(C_{1-3}$ alkyl)NH, $(C_{1-3}$ alkyl)$_2$N, $(H_2NCH_2C(O))NH$, $(H_2NCH(CH_3)C(O))NH$, $(CH_3NHCH_2C(O))NH$, $((CH_3)_2NCH_2C(O))NH$, $CF_3$, $OCF_3$, —CN, $NO_2$, $C(O)NH_2$, and $CH_3C(O)NH$;

Y is selected from phenyl substituted with 0–5 $R^b$, naphthyl substituted with 0–5 $R^b$, and $CHR^3$;

$R^b$ is selected from H, Cl, F, Br, I, $C_{1-4}$ alkyl, OH, $C_{1-4}$ alkoxy, $CH_2OH$, $CH(OH)CH_3$, $CF_3$, $OCF_3$, —CN, $NO_2$, $NH_2$, $(C_{1-3}$ alkyl)NH, $(C_{1-3}$ alkyl)$_2$N, and $C(O)O—C_{1-4}$ alkoxy;

$R^2$ is selected from H, $R^{2a}$, C(O)$R^{2a}$, CH(OH)$R^{2a}$, CH$_2$$R^{2a}$, O$R^{2a}$, S$R^{2a}$, and NH$R^{2a}$;

$R^{2a}$ is selected from phenyl, naphthyl, and a 5–6 membered heteroaryl ring with 1–4 heteroatoms selected from N, NH, O, and S, and $R^{2a}$ is substituted with 0–5 $R^b$;

$R^3$ is phenyl substituted with 0–2 $R^c$ or naphthyl substituted with 0–2 $R^c$; and, $R^c$ is selected from H, Cl, F, Br, I, C$_{1-4}$ alkyl, OH, C$_{1-4}$ alkoxy, CH$_2$OH, CH(OH)CH$_3$, CF$_3$, OCF$_3$, —CN, NO$_2$, NH$_2$, (C$_{1-3}$ alkyl)NH, (C$_{1-3}$ alkyl)$_2$N, and C(O)O—C$_{1-4}$ alkoxy.

In a preferred embodiment, the present invention provides a novel compound, wherein:

$R^1$ is phenyl or a 5–6 membered heteroaryl ring with 1–2 heteroatoms selected from N, NH, O, and S, and $R^1$ is substituted with 0–2 $R^a$;

$R^a$ is selected from H, Cl, F, C$_{1-4}$ alkyl, C$_{1-4}$ alkoxy, OH, CH$_2$OH, NH$_2$, (C$_{1-3}$ alkyl)NH, (C$_{1-3}$ alkyl)$_2$N, (H$_2$NCH$_2$C(O))NH, (H$_2$NCH(CH$_3$)C(O))NH, (CH$_3$NHCH$_2$C(O))NH, ((CH$_3$)$_2$NCH$_2$C(O))NH, and CH$_3$C(O)NH;

Y is selected from phenyl substituted with 0–5 $R^b$, naphthyl substituted with 0–5 $R^b$, and CH$R^3$;

$R^b$ is selected from H, Cl, F, Br, C$_{1-4}$ alkyl, OH, C$_{1-4}$ alkoxy, CH$_2$OH, CH(OH)CH$_3$, CF$_3$, —CN, NO$_2$, NH$_2$, and (C$_{1-3}$ alkyl)NH, (C$_{1-3}$ alkyl)$_2$N;

$R^2$ is selected from H, $R^{2a}$, C(O)$R^{2a}$, CH(OH)$R^{2a}$, CH$_2$$R^{2a}$, and O$R^{2a}$;

$R^{2a}$ is selected from phenyl, naphthyl, and a 5–6 membered heteroaryl ring with 1–4 heteroatoms selected from N, NH, O, and S, and $R^{2a}$ is substituted with 0–5 $R^b$;

$R^3$ is phenyl substituted with 0–2 $R^c$ or naphthyl substituted with 0–2 $R^c$; and, $R^c$ is selected from H, Cl, F, Br, I, C$_{1-4}$ alkyl, OH, C$_{1-4}$ alkoxy, CH$_2$OH, CH(OH)CH$_3$, CF$_3$, —CN, NO$_2$, NH$_2$, (C$_{1-3}$ alkyl)NH, and (C$_{1-3}$ alkyl)$_2$N.

In a more preferred embodiment, the present invention provides a novel compound, wherein:

$R^1$ is phenyl or a 5–6 membered heteroaryl ring with 1–2 heteroatoms selected from N, NH, O, and S, and $R^1$ is substituted with 0–2 $R^a$;

$R^a$ is selected from H, OH, and NH$_2$;

Y is selected from phenyl substituted with 0–2 $R^b$, naphthyl substituted with 0–2 $R^b$, and CH$R^3$;

$R^b$ is selected from H, Cl, F, Br, C$_{1-4}$ alkyl, OH, C$_{1-4}$ alkoxy, CH$_2$OH, CH(OH)CH$_3$, CF$_3$, —CN, NO$_2$, NH$_2$, and (C$_{1-3}$ alkyl)NH, (C$_{1-3}$ alkyl)$_2$N;

$R^2$ is selected from H, $R^{2a}$, C(O)$R^{2a}$, CH(OH)$R^{2a}$, CH$_2$$R^{2a}$, and O$R^{2a}$;

$R^{2a}$ is selected from phenyl, naphthyl, and a 5–6 membered heteroaryl ring with 1–4 heteroatoms selected from N, NH, O, and S, and $R^{2a}$ is substituted with 0–5 $R^b$;

$R^3$ is phenyl substituted with 0–2 $R^c$ or naphthyl substituted with 0–2 $R^c$; and, $R^c$ is selected from H, Cl, F, Br, I, C$_{1-4}$ alkyl, OH, C$_{1-4}$ alkoxy, CH$_2$OH, CH(OH)CH$_3$, CF$_3$, —CN, NO$_2$, NH$_2$, (C$_{1-3}$ alkyl)NH, and (C$_{1-3}$ alkyl)$_2$N.

In an even more preferred embodiment, the present invention provides a novel compound selected from:

E- and Z-α-[amino[(2-aminophenyl)thio]methylene]-4-chloro-2-methyl-β-phenylbenzenepropanenitrile;

E- and Z-α-[amino[(2-aminophenyl)thio]methylene]-3-[(2,4-dinitrophenyl)hydroxymethyl]benzeneacetonitrile;

E- and Z-α-[amino[(2-aminophenyl)thio]methylene]-3-[(4-carbomethoxyphenyl)hydroxymethyl]benzeneacetonitrile;

E- and Z-α-[amino[(2-aminophenyl)thio]methylene]-3-[(4-nitrophenyl)hydroxymethyl]benzeneacetonitrile;

E- and Z-α-[amino[(2-aminophenyl)thio]methylene]-3-[(pentafluorophenyl)hydroxymethyl]benzeneacetonitrile;

E- and Z-α-[amino[(2-aminophenyl)thio]methylene]-2-methyl-3-[(4-pyridyl)hydroxymethyl]benzeneacetonitrile;

E- and Z-α-[amino[(2-aminophenyl)thio]methylene]-2-methyl-3-[(phenyl)hydroxymethyl]benzeneacetonitrile;

E- and Z-α-[amino[(2-aminophenyl)thio]methylene]-2-methyl-3-[(4-pyridyl)hydroxymethyl]benzeneacetonitrile;

E- and Z-α-[amino[(2-hydroxyphenyl)thio]methylene]-3-[(4-cyanophenyl)hydroxymethyl]benzeneacetonitrile;

E- and Z-α-[amino[(2-aminophenyl)thio]methylene]-3-[(3-nitrophenyl)hydroxymethyl]benzeneacetonitrile;

E- and Z-α-[amino[(2-aminophenyl)thio]methylene]-2-methyl-3-[(pentafluorophenyl)hydroxymethyl]benzeneacetonitrile;

E- and Z-α-[amino[(2-hydroxyphenyl)thio]methylene]-3-[(4-pyridyl)hydroxymethyl]benzeneacetonitrile;

E- and Z-α-[amino[(2-aminophenyl)thio]methylene]-3-[(2-trifluoromethylphenyl)hydroxymethyl]benzeneacetonitrile E- and Z-α-[amino[(4-aminophenyl)thio]methylene]-3-[(4-pyridyl)hydroxymethyl]benzeneacetonitrile;

E- and Z-α-[amino[(4-hydroxyphenyl)thio]methylene]-3-[(4-pyridyl)hydroxymethyl]benzeneacetonitrile;

E- and Z-α-[amino[(2-aminophenyl)thio]methylene]-3-[(3-cyanophenyl)hydroxymethyl]benzeneacetonitrile;

E- and Z-α-[amino[(4-aminophenyl)thio]methylene]-3-[(4-cyanophenyl)hydroxymethyl]benzeneacetonitrile;

E- and Z-α-[amino(phenylthio)methylene]-3-[(4-cyanophenyl)hydroxymethyl]benzeneacetonitrile;

E- and Z-α-[amino(phenylthio)methylene]-3-[(4-pyridyl)hydroxymethyl]benzeneacetonitrile;

E- and Z-α-[amino[(4-aminophenyl)thio]methylene]-2-bromobenzeneacetonitrile;

E- and Z-α-[amino[(2-aminophenyl)thio]methylene]-3-[(2,4-dimethylphenyl)hydroxymethyl]benzeneacetonitrile;

E- and Z-α-[amino[(2-aminophenyl)thio]methylene]-3-[(phenyl)hydroxymethyl]benzeneacetonitrile;

E- and Z-α-[amino[(2-aminophenyl)thio]methylene]-3-[(2-thienyl)hydroxymethyl]benzeneacetonitrile;

E- and Z-α-[amino[(2-aminophenyl)thio]methylene]-4-chloro-β-phenylbenzenepropanenitrile;

E- and Z-α-[amino[(2-thienyl)thio]methylene]-3-[(phenyl)hydroxymethyl]benzeneacetonitrile;

E- and Z-α-[amino[(2,4-diaminophenyl)thio]methylene]-1-naphthyleneacetonitrile;

E- and Z-α-[amino[(2-aminophenyl)thio]methylene]-2-methyl-β-(4-pyridyl)benzenepropanenitrile;

E- and Z-α-[amino[(4-aminophenyl)thio]methylene]-3-(benzyl)benzeneacetonitrile;

E- and Z-α-[amino[(2-naphthyl)thio]methylene]-1-naphthyleneacetonitrile;

E- and Z-α-[amino[(2-aminophenyl)thio]methylene]-3-(benzoyl)benzeneacetonitrile;

E- and Z-α-[amino[(2-aminophenyl)thio]methylene]-β-(1-methyl-2-pyrrolyl)benzenepropanenitrile;

E- and Z-α-[amino[(2-aminophenyl)thio]methylene]-3-phenoxybenzeneacetonitrile;

E- and Z-α-[amino[(2-aminophenyl)thio]methylene]-2-bromobenzeneacetonitrile;

E- and Z-α-[amino[(2-aminophenyl)thio]methylene]-3-[(2-furanyl)hydroxymethyl]benzeneacetonitrile;

E- and Z-α-[amino[(2-thienyl)thio]methylene]-3-[(2,3,4,5,6-pentafluorophenyl)hydroxymethyl]benzeneacetonitrile;

E- and Z-α-[amino[(2-aminophenyl)thio]methylene]-3-[(3-methyl-2-pyridyl)hydroxymethyl]benzeneacetonitrile;

E- and Z-α-[amino[(4-aminophenyl)thio]methylene]-2-methylbenzeneacetonitrile;

E- and Z-α-[amino[(4-aminophenyl)thio]methylene]-4-(1,1-dimethylethyl)benzeneacetonitrile;

E- and Z-α-[amino[(4-aminophenyl)thio]methylene]-1-naphthyleneacetonitrile;

E- and Z-α-[amino[(2-aminophenyl)thio]methylene]-3-(trifluoromethyl)benzeneacetonitrile;

E- and Z-α-[amino[(2-aminophenyl)thio]methylene]-1-naphthyleneacetonitrile;

E- and Z-α-[amino[(2-aminophenyl)thio]methylene]-2-(trifluoromethyl)benzeneacetonitrile;

E- and Z-α-[amino[(4-aminophenyl)thio]methylene]-4-methylbenzeneacetonitrile;

E- and Z-α-[amino[(2-aminophenyl)thio]methylene]-2-methylbenzeneacetonitrile;

E- and Z-α-[amino[(2-fluorophenyl)thio]methylene]-1-naphthyleneacetonitrile; and, E- and Z-α-[amino[(2-aminophenyl)thio]methylene]-3-phenyl benzeneacetonitrile;

or a pharmaceutically acceptable salt form thereof.

In a further preferred embodiment, the present invention provides a novel compound selected from:

E-α-[amino[(2-aminophenyl)thio]methylene]-4-chloro-2-methyl-β-phenylbenzenepropanenitrile;

E-α-[amino[(2-aminophenyl)thio]methylene]-3-[(2,4-dinitrophenyl)hydroxymethyl]benzeneacetonitrile;

E-α-[amino[(2-aminophenyl)thio]methylene]-3-[(4-carbomethoxyphenyl)hydroxymethyl]benzeneacetonitrile;

E-α-[amino[(2-aminophenyl)thio]methylene]-3-[(4-nitrophenyl)hydroxymethyl]benzeneacetonitrile;

E-α-[amino[(2-aminophenyl)thio]methylene]-3-[(pentafluorophenyl)hydroxymethyl]benzeneacetonitrile;

E-α-[amino[(2-aminophenyl)thio]methylene]-2-methyl-3-[(4-pyridyl)hydroxymethyl]benzeneacetonitrile;

E-α-[amino[(2-aminophenyl)thio]methylene]-2-methyl-3-[(phenyl)hydroxymethyl]benzeneacetonitrile;

E-α-[amino[(2-aminophenyl)thio]methylene]-2-methyl-3-[(4-pyridyl)hydroxymethyl]benzeneacetonitrile;

E-α-[amino[(2-hydroxyphenyl)thio]methylene]-3-[(4-cyanophenyl)hydroxymethyl]benzeneacetonitrile;

E-α-[amino[(2-aminophenyl)thio]methylene]-3-[(3-nitrophenyl)hydroxymethyl]benzeneacetonitrile;

E-α-[amino[(2-aminophenyl)thio]methylene]-2-methyl-3-[(pentafluorophenyl)hydroxymethyl]benzeneacetonitrile;

E-α-[amino[(2-hydroxyphenyl)thio]methylene]-3-[(4-pyridyl)hydroxymethyl]benzeneacetonitrile;

E-α-[amino[(2-aminophenyl)thio]methylene]-3-[(2-trifluoromethylphenyl)hydroxymethyl]benzeneacetonitrile E-α-[amino[(4-aminophenyl)thio]methylene]-3-[(4-pyridyl)hydroxymethyl]benzeneacetonitrile;

E-α-[amino[(4-hydroxyphenyl)thio]methylene]-3-[(4-pyridyl)hydroxymethyl]benzeneacetonitrile;

E-α-[amino[(2-aminophenyl)thio]methylene]-3-[(3-cyanophenyl)hydroxymethyl]benzeneacetonitrile;

E-α-[amino[(4-aminophenyl)thio]methylene]-3-[(4-cyanophenyl)hydroxymethyl]benzeneacetonitrile;

E-α-[amino(phenylthio)methylene]-3-[(4-cyanophenyl)hydroxymethyl]benzeneacetonitrile;

E-α-[amino(phenylthio)methylene]-3-[(4-pyridyl)hydroxymethyl]benzeneacetonitrile;

E-α-[amino[(4-aminophenyl)thio]methylene]-2-bromobenzeneacetonitrile;

E-α-[amino[(2-aminophenyl)thio]methylene]-3-[(2,4-dimethylphenyl)hydroxymethyl]benzeneacetonitrile;

E-α-[amino[(2-aminophenyl)thio]methylene]-3-[(phenyl)hydroxymethyl]benzeneacetonitrile;

E-α-[amino[(2-aminophenyl)thio]methylene]-3-[(2-thienyl)hydroxymethyl]benzeneacetonitrile;

E-α-[amino[(2-aminophenyl)thio]methylene]-4-chloro-β-phenylbenzenepropanenitrile;

E-α-[amino[(2-thienyl)thio]methylene]-3-[(phenyl)hydroxymethyl]benzeneacetonitrile;

E-α-[amino[(2,4-diaminophenyl)thio]methylene]-1-naphthyleneacetonitrile;

E-α-[amino[(2-aminophenyl)thio]methylene]-2-methyl-β-(4-pyridyl)benzenepropanenitrile;

E-α-[amino[(4-aminophenyl)thio]methylene]-3-(benzyl)benzeneacetonitrile;

E-α-[amino[(2-naphthyl)thio]methylene]-1-naphthyleneacetonitrile;

E-α-[amino[(2-aminophenyl)thio]methylene]-3-(benzoyl)benzeneacetonitrile;

E-α-[amino[(2-aminophenyl)thio]methylene]-β-(1-methyl-2-pyrrolyl)benzenepropanenitrile;

E-α-[amino[(2-aminophenyl)thio]methylene]-3-phenoxybenzeneacetonitrile;

E-α-[amino[(2-aminophenyl)thio]methylene]-2-bromobenzeneacetonitrile;

E-α-[amino[(2-aminophenyl)thio]methylene]-3-[(2-furanyl)hydroxymethyl]benzeneacetonitrile;

E-α-[amino[(2-thienyl)thio]methylene]-3-[(2,3,4,5,6-pentafluorophenyl)hydroxymethyl]benzeneacetonitrile;

E-α-[amino[(2-aminophenyl)thio]methylene]-3-[(3-methyl-2-pyridyl)hydroxymethyl]benzeneacetonitrile;

E-α-[amino[(4-aminophenyl)thio]methylene]-2-methylbenzeneacetonitrile;

E-α-[amino[(4-aminophenyl)thio]methylene]-4-(1,1-dimethylethyl)benzeneacetonitrile;

E-α-[amino[(4-aminophenyl)thio]methylene]-1-naphthyleneacetonitrile;

E-α-[amino[(2-aminophenyl)thio]methylene]-3-(trifluoromethyl)benzeneacetonitrile;

E-α-[amino[(2-aminophenyl)thio]methylene]-1-naphthyleneacetonitrile;

E-α-[amino[(2-aminophenyl)thio]methylene]-2-(trifluoromethyl)benzeneacetonitrile;

E-α-[amino[(4-aminophenyl)thio]methylene]-4-methylbenzeneacetonitrile;

E-α-[amino[(2-aminophenyl)thio]methylene]-2-methylbenzeneacetonitrile;

E-α-[amino[(2-fluorophenyl)thio]methylene]-1-naphthyleneacetonitrile; and,

E-α-[amino[(2-aminophenyl)thio]methylene]-3-phenyl benzeneacetonitrile;

or a pharmaceutically acceptable salt form thereof.

In a further preferred embodiment, the present invention provides a novel compound selected from:

Z-α-[amino[(2-aminophenyl)thio]methylene]-4-chloro-2-methyl-β-phenylbenzenepropanenitrile;

Z-α-[amino[(2-aminophenyl)thio]methylene]-3-[(2,4-dinitrophenyl)hydroxymethyl]benzeneacetonitrile;
Z-α-[amino[(2-aminophenyl)thio]methylene]-3-[(4-carbomethoxyphenyl)hydroxymethyl]benzeneacetonitrile;
Z-α-[amino[(2-aminophenyl)thio]methylene]-3-[(4-nitrophenyl)hydroxymethyl]benzeneacetonitrile;
Z-α-[amino[(2-aminophenyl)thio]methylene]-3-[(pentafluorophenyl)hydroxymethyl]benzeneacetonitrile;
Z-α-[amino[(2-aminophenyl)thio]methylene]-2-methyl-3-[(4-pyridyl)hydroxymethyl]benzeneacetonitrile;
Z-α-[amino[(2-aminophenyl)thio]methylene]-2-methyl-3-[(phenyl)hydroxymethyl]benzeneacetonitrile;
Z-α-[amino[(2-aminophenyl)thio]methylene]-2-methyl-3-[(4-pyridyl)hydroxymethyl]benzeneacetonitrile;
Z-α-[amino[(2-hydroxyphenyl)thio]methylene]-3-[(4-cyanophenyl)hydroxymethyl]benzeneacetonitrile;
Z-α-[amino[(2-aminophenyl)thio]methylene]-3-[(3-nitrophenyl)hydroxymethyl]benzeneacetonitrile;
Z-α-[amino[(2-aminophenyl)thio]methylene]-2-methyl-3-[(pentafluorophenyl)hydroxymethyl]benzeneacetonitrile;
Z-α-[amino[(2-hydroxyphenyl)thio]methylene]-3-[(4-pyridyl)hydroxymethyl]benzeneacetonitrile;
Z-α-[amino[(2-aminophenyl)thio]methylene]-3-[(2-trifluoromethylphenyl)hydroxymethyl]benzeneacetonitrile
Z-α-[amino[(4-aminophenyl)thio]methylene]-3-[(4-pyridyl)hydroxymethyl]benzeneacetonitrile;
Z-α-[amino[(4-hydroxyphenyl)thio]methylene]-3-[(4-pyridyl)hydroxymethyl]benzeneacetonitrile;
Z-α-[amino[(2-aminophenyl)thio]methylene]-3-[(3-cyanophenyl)hydroxymethyl]benzeneacetonitrile;
Z-α-[amino[(4-aminophenyl)thio]methylene]-3-[(4-cyanophenyl)hydroxymethyl]benzeneacetonitrile;
Z-α-[amino(phenylthio)methylene]-3-[(4-cyanophenyl)hydroxymethyl]benzeneacetonitrile;
Z-α-[amino(phenylthio)methylene]-3-[(4-pyridyl)hydroxymethyl]benzeneacetonitrile;
Z-α-[amino[(4-aminophenyl)thio]methylene]-2-bromobenzeneacetonitrile;
Z-α-[amino[(2-aminophenyl)thio]methylene]-3-[(2,4-dimethylphenyl)hydroxymethyl]benzeneacetonitrile;
Z-α-[amino[(2-aminophenyl)thio]methylene]-3-[(phenyl)hydroxymethyl]benzeneacetonitrile;
Z-α-[amino[(2-aminophenyl)thio]methylene]-3-[(2-thienyl)hydroxymethyl]benzeneacetonitrile;
Z-α-[amino[(2-aminophenyl)thio]methylene]-4-chloro-β-phenylbenzenepropanenitrile;
Z-α-[amino[(2-thienyl)thio]methylene]-3-[(phenyl)hydroxymethyl]benzeneacetonitrile;
Z-α-[amino[(2,4-diaminophenyl)thio]methylene]-1-naphthyleneacetonitrile;
Z-α-[amino[(2-aminophenyl)thio]methylene]-2-methyl-β-(4-pyridyl)benzenepropanenitrile;
Z-α-[amino[(4-aminophenyl)thio]methylene]-3-(benzyl)benzeneacetonitrile;
Z-α-[amino[(2-naphthyl)thio]methylene]-1-naphthyleneacetonitrile;
Z-α-[amino[(2-aminophenyl)thio]methylene]-3-(benzoyl)benzeneacetonitrile;
Z-α-[amino[(2-aminophenyl)thio]methylene]-β-(1-methyl-2-pyrrolyl)benzenepropanenitrile;
Z-α-[amino[(2-aminophenyl)thio]methylene]-3-phenoxybenzeneacetonitrile;
Z-α-[amino[(2-aminophenyl)thio]methylene]-2-bromobenzeneacetonitrile;
Z-α-[amino[(2-aminophenyl)thio]methylene]-3-[(2furanyl)hydroxymethyl]benzeneacetonitrile;
Z-α-[amino[(2-thienyl)thio]methylene]-3-[(2,3,4,5,6-pentafluorophenyl)hydroxymethyl]benzeneacetonitrile;
Z-α-[amino[(2-aminophenyl)thio]methylene]-3-[(3-methyl-2-pyridyl)hydroxymethyl]benzeneacetonitrile;
Z-α-[amino[(4-aminophenyl)thio]methylene]-2-methylbenzeneacetonitrile;
Z-α-[amino[(4-aminophenyl)thio]methylene]-4-(1,1-dimethylethyl)benzeneacetonitrile;
Z-α-[amino[(4-aminophenyl)thio]methylene]-1-naphthyleneacetonitrile;
Z-α-[amino[(2-aminophenyl)thio]methylene]-3-(trifluoromethyl)benzeneacetonitrile;
Z-α-[amino[(2-aminophenyl)thio]methylene]-1-naphthyleneacetonitrile;
Z-α-[amino[(2-aminophenyl)thio]methylene]-2-(trifluoromethyl)benzeneacetonitrile;
Z-α-[amino[(4-aminophenyl)thio]methylene]-4-methylbenzeneacetonitrile;
Z-α-[amino[(2-aminophenyl)thio]methylene]-2-methylbenzeneacetonitrile;
Z-α-[amino[(2-fluorophenyl)thio]methylene]-1-naphthyleneacetonitrile; and,
Z-α-[amino[(2-aminophenyl)thio]methylene]-3-phenyl benzeneacetonitrile;

or a pharmaceutically acceptable salt form thereof.

In another embodiment, the present invention provides novel pharmaceutical compositions, comprising: a pharmaceutically acceptable carrier and a therapeutically effective amount of a compound of formula Ia or Ib or a pharmaceutically acceptable salt form thereof.

In another embodiment, the present invention provides a novel method for treating or preventing a disorder related to MEK, comprising: administering to a patient in need thereof a therapeutically effective amount of a compound of formula Ia or Ib or a pharmaceutically acceptable salt form thereof.

In another embodiment, the present invention provides novel compounds of formula Ia or Ib or a pharmaceutically acceptable salt form thereof for use in therapy.

In another embodiment, the present invention provides novel compounds of formula Ia or Ib or a pharmaceutically acceptable salt form thereof for the manufacture of a medicament for the treatment of an inflammatory disease.

In another embodiment, the present invention provides novel compounds of formula Ia or Ib or a pharmaceutically acceptable salt form thereof for the manufacture of a medicament for the treatment of cancer.

In another embodiment, the present invention provides a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-4}$ alkyl is intended to include $C_1$, $C_2$, $C_3$, and $C_4$ alkyl. Examples of alkyl include, but are not limited to, methyl, ethyl, n-propyl, i-propyl, n-butyl, s-butyl, t-butyl, n-pentyl, and s-pentyl. "Alkoxy" represents an alkyl group as defined above with the indicated number of carbon atoms attached through an oxygen bridge. $C_{1-4}$ alkoxy is intended to include $C_1$, $C_2$, $C_3$, and $C_4$, alkoxy. Examples of alkoxy include, but are not limited to, methoxy, ethoxy, n-propoxy, i-propoxy, n-butoxy, s-butoxy, t-butoxy, n-pentoxy, and s-pentoxy.

As used herein, the term "aromatic heterocyclic system" or "heteroaryl" is intended to mean a stable 5 or 6 membered monocyclic aromatic ring which consists of carbon atoms and 1, 2, 3, or 4 heterotams independently selected from the group consisting of N, NH, O and S. It is to be noted that that the total number of S and O atoms in an aromatic heterocycle is not more than 1.

Examples of heterocycles include, but are not limited to, 2H,6H-1,5,2-dithiazinyl, furanyl, imidazolyl, isothiazolyl, isoxazolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, pyranyl, pyrazinyl, pyrazolidinyl, pyrazolinyl, pyrazolyl, pyridazinyl, pyridyl, 2H-pyrrolyl, pyrrolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, triazinyl, 1,2,3-triazolyl, 1,2,4-triazolyl, 1,2,5-triazolyl, and 1,3,4-triazolyl. Preferred heterocycles include, but are not limited to, pyridinyl, furanyl, thienyl, pyrrolyl, pyrazolyl, and imidazolyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula Ia or Ib in vivo when such prodrug is administered to a mammalian subject. Prodrugs of a compound of formula Ia or Ib are prepared by modifying functional groups present in the compound in such a way that the modifications are cleaved, either in routine manipulation or in vivo, to the parent compound. Prodrugs include compounds of formula Ia or Ib wherein a hydroxy, amino, or sulfhydryl group is bonded to any group that, when the prodrug or compound of formula Ia or Ib is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula Ia or Ib.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit MEK or treat the symptoms of MEK over production in a host. The combination of compounds is preferably a synergistic combination. Synergy, as described for example by Chou and Talalay, Adv. Enzyme Regul. 22:27–55 (1984), occurs when the effect (in this case, MEK inhibition) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

The term "radiosensitize", as used herein refers to a process whereby cells are made susceptible to radiation-induced cell death, or the cells that result from the process.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Compounds of the present invention (3) may be synthesized by the route described in Scheme 1. A thiol 1, such as a thiophenol, may be treated with a malononitrile such as malononitrile 2 in the presence of a base catalyst such as triethylamine, DBU, Hunig's base, or aqueous base (for example, 10% NaOH), etc., in a nonreactive solvent such as THF, acetone, etc., to yield the vinylogous cyanamide 3. The reaction medium can be degassed to eliminate the presence of oxygen which can facilitate disulfide formation via the dimerization of thiol 1. The vinylogous cyanamide is frequently isolated as a mixture of Z- and E-isomers and the melting point varies significantly with isomer composition. A crystalline single isomer or material enriched in one isomer may sometimes be obtained by spontaneous crystallization of one isomer, recrystallization, or stirring solid in a solvent which dissolves only part of the material. Alternatively, isomers may sometimes be separated by chromatography. However, the double bond in 3 isomerizes very easily. NMR spectroscopy of a single isomer in DMSO-$d_6$ shows that an equilibrium mixture of Z- and E-isomers is generated faster than the spectrum could be obtained (about 5 minutes). Isomerization also takes place in other solvents such as water, acetone, methanol, and chloroform, but more slowly than in DMSO. Rapid NMR in one of these solvents may be used to establish isomeric composition. For in vitro assays, the compounds may be dissolved in DMSO to ensure that an equilibrium mixture of isomers is tested.

Scheme 1: Preparation of vinylogous cyanamides

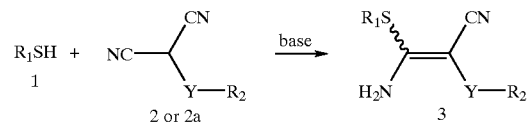

Many thiols (1) are commercially available. Alternatively, there are many methods for their synthesis familiar to one skilled in the art. For example, aryl or heterocyclic anions may be quenched with sulfur to yield thiols (*Chem. Pharm. Bull.* 1989, 37 (1), 36). Displacement of aryldiazonium salts with $EtOCS_2K$ leads to aryl thiols (*Collect. Czech. Chem. Commun.* 1990, 55, 1266). The Newman rearrangement of phenols via their dimethylthiocarbamates leads to thiophenols (*Organic Syntheses VI*, (1988) 824).

When the Y group in Scheme 1 is substituted phenyl or naphthyl, the malononitrile precursors (2) to the compounds of this invention may be prepared by one of the three routes shown in Scheme 2. In the first route, aryl iodides 4 may be treated with malononitrile in the presence of a copper catalyst to yield arylmalononitriles 2 (*J. Org. Chem.* 1993 (58) 7606–7). Malononitrile can also be coupled to aryl halides 4 (X=halide) using. $(Ph_3P)_2PdCl_2$ or $Pd(Ph_3P)_4$ in THF (*J. Chem. Soc. Chem. Comm.* 1984, 932–3). The aryl iodides needed for these methods are commercially available or prepared by methods familiar to one skilled in the art. In particular, aryl iodides may be prepared by iodination with a source of electrophilic iodine, such as iodine monochloride, or by diazotization of anilines.

Scheme 2:
Preparation of malononitriles 2 when Y is a substituted phenyl or naphthy

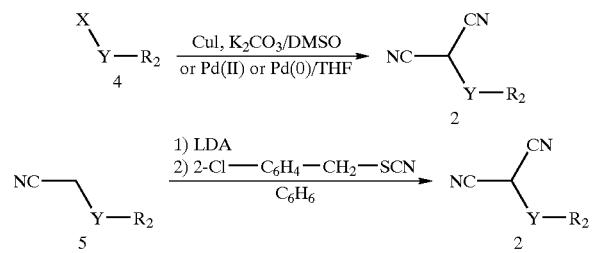

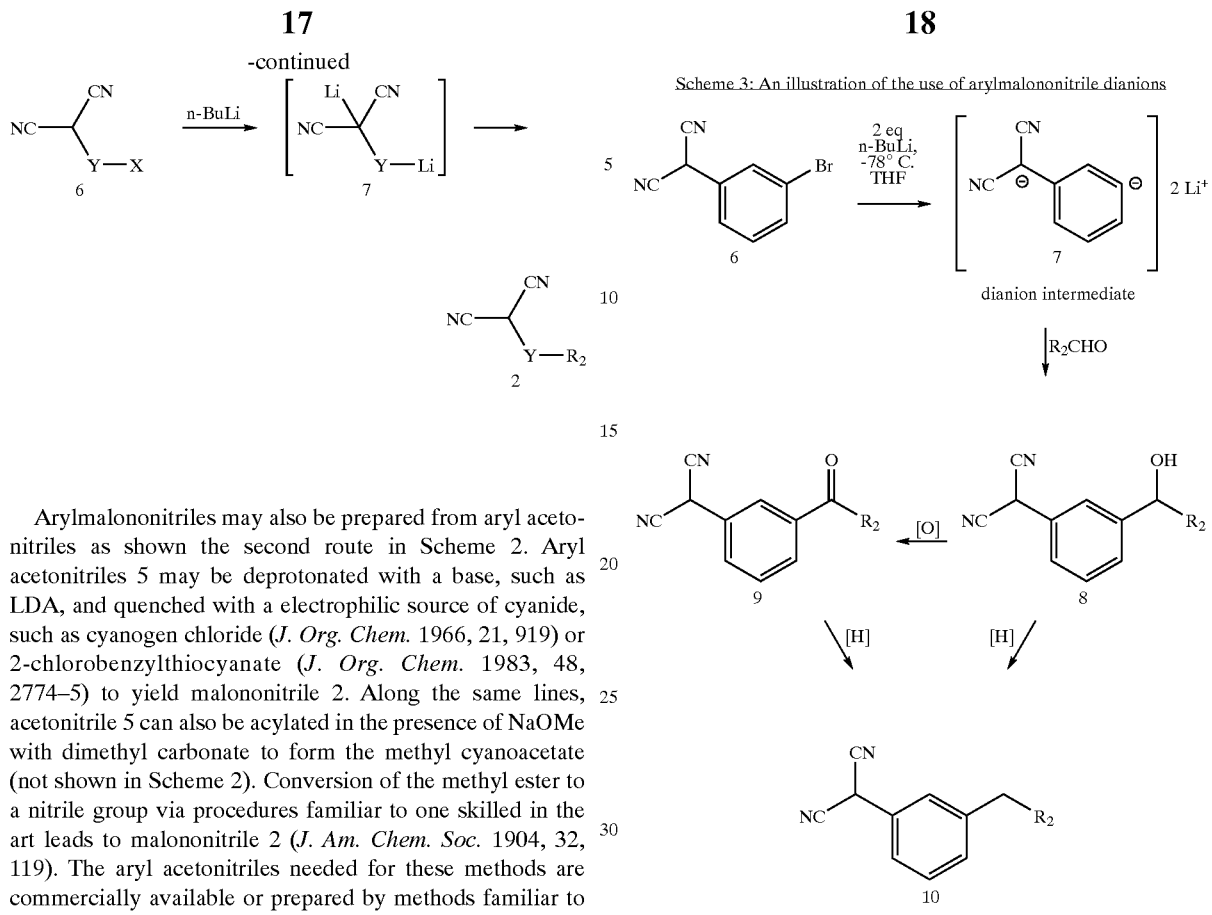

Arylmalononitriles may also be prepared from aryl acetonitriles as shown the second route in Scheme 2. Aryl acetonitriles 5 may be deprotonated with a base, such as LDA, and quenched with a electrophilic source of cyanide, such as cyanogen chloride (*J. Org. Chem.* 1966, 21, 919) or 2-chlorobenzylthiocyanate (*J. Org. Chem.* 1983, 48, 2774–5) to yield malononitrile 2. Along the same lines, acetonitrile 5 can also be acylated in the presence of NaOMe with dimethyl carbonate to form the methyl cyanoacetate (not shown in Scheme 2). Conversion of the methyl ester to a nitrile group via procedures familiar to one skilled in the art leads to malononitrile 2 (*J. Am. Chem. Soc.* 1904, 32, 119). The aryl acetonitriles needed for these methods are commercially available or prepared by methods familiar to one skilled in the art, for example, from aryl acetamides or from toluenes. When $R_2$ is an optionally substituted phenoxy group, the initial step in the preparation of the compounds of this invention may be an Ullmann condensation between an aryl halide and a phenol. (For useful protocols, see: U.S. Pat. No. 4,288,386; and *Tetrahedron* (1961), 15, 144–153.) A methyl substituent on either of these substrates may be subsequently converted to a —$CH_2CN$ group by free radical halogenation, with a reagent such as N-bromosuccinimide, followed by displacement with cyanide.

As shown in the third route shown in Scheme 2, arylmalononitriles 2 may also be synthesized from simpler bromo- or iodoarylmalononitriles. These bromo- or iodo-substituted arylmalononitriles may be prepared by either of the first two routes indicated in Scheme 2 for the preparation of malononitriles. Bromo- or iodo-substituted arylmalononitriles undergo halogen-metal exchange in the presence of two or more equivalents of an alkyllithium reagent, such as n-butyllithium, to form dianion intermediate 7. This process may be carried out in an ethereal solvent such as THF at a temperature of –78 to 0° C. The dianion may be quenched in situ with one equivalent of an electrophile, such as an aldehyde, alkyl halide, disulfide, ester, or ketone, to yield a substituted malononitrile 2 with a new $R_2$ group attached to the former site of the bromine or iodine atom. This is process is illustrated in more detail in Scheme 3 for the case where Y is a 1,3-disubstituted phenyl group. 3-Bromophenylmalononitrile (6) may be converted to dianion 7a by deprotonation and halogen-metal exchange with 2 equivalents of n-butyllithium in THF at –78° C. The dianion may be treated in situ with an aldehyde to produce hydroxy-phenylmalononitriles 8. Hydroxy-phenylmalononitriles 8 may be oxidized to the corresponding keto-phenylmalononitrile 9 using $MnO_2$ or a variety of other oxidizing agents familiar to one skilled in the art. Compounds 8 and 9 may be reduced to the corresponding $CH_2R_2$-substituted phenylmalononitriles 10 using hydrogen and a noble metal catalyst, $NaBH_4$ and TFA (*Synthesis* 1978, 763–5), or other procedures familiar to one skilled in the art. Malononitriles 8, 9, and 10 may be treated with thiols 1 to yield the compounds of this invention. It must be noted that although only the meta-bromo isomer of 6 is pictured in Scheme 3, one trained in the art may apply this methodology using other aryl halides and electrophiles to prepare isomers and compounds with different Y groups.

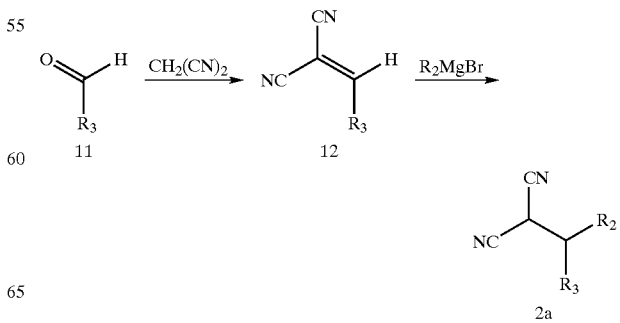

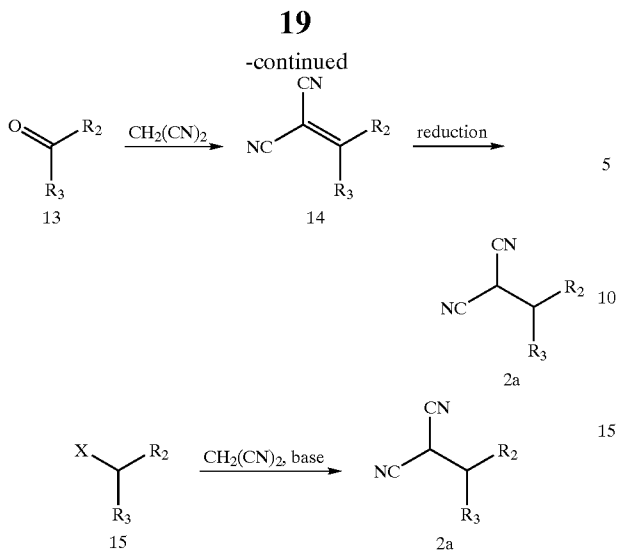

When Y is CHR$_3$, malononitrile precursors useful for preparation of the compounds of this invention have structure 2a and may be prepared as shown in Scheme 4. Knoevenagel condensation (*Organic Reactions* 15, 204–509 (1967)) between an aldehyde 11 or a ketone 13 may be used to produce alkylidene malononitriles 12 or 14. Conjugate addition of a Grignard or organolithium reagent to 12 affords the malononitrile prescursors 2 used in Scheme 1. Alternatively, alkylidene malononitriles 14 may be reduced to malononitriles 2a with sodium borohydride, catalytic hydrogenation or other reducing agents familiar to one skilled in the art. A third alternative is to alkylate malononitrile with an alkyl halide 15 (X=halide).

Other features of the invention will become apparent in the course of the following descriptions of exemplary embodiments which are given for illustration of the invention and are not intended to be limiting thereof.

EXAMPLES

Abbreviations used in the Examples are defined as follows: "1 x" for once, "2 x" for twice, "3 x" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

Z- and E-α-[amino[(4-aminophenyl)thio]methylene]-2-(trifluoromethyl)benzeneacetonitrile

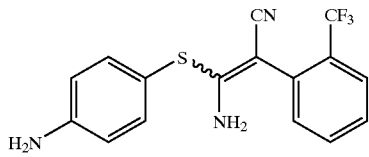

Part A. Preparation of 2-[(2-trifluoromethyl)phenyl]malononitrile

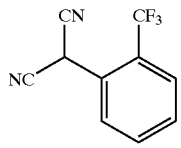

A mixture of 2-trifluoromethyl-1-iodobenzene (21.76 g, 0.08 mol, 1 eq), malononitrile (10.56 g, 0.16 mol, 2 eq), copper(I) iodide (1.52 g, 0.008 mol, 0.1 eq), potassium carbonate (11.04 g, 0.32 mol, 4 eq), and 200 mL DMSO was stirred and heated at 120° C. for 21 h. The reaction mixture was cooled and poured into 1.2 L of 0.5 M HCl. The mixture was filtered and extracted with ethyl acetate. The organic layer was dried (MgSO$_4$) and the solvent removed in vacuo to yield an oil. This oil was purified by flash chromatography on silica gel with 3:1 hexane/ethyl acetate to yield 4.46 g (27%) of 2-[(2-trifluoromethyl)phenyl]malononitrile as a yellow oil. $^1$H-NMR (CDCl$_3$) δ: 8.05–7.10 (m, 4H); 5.30 (s, 1H).

Part B. Preparation of α-[amino[(4-aminophenyl)thio]methylene]-2-(trifluoromethyl)benzeneacetonitrile 2-[(2-Trifluoromethyl)phenyl]malononitrile (the product from Part A) (3.07 g, 14.6 mmol, 1.1 eq), freshly distilled 4-aminothiophenol (1.66 g, 13.3 mmol, 1 eq), and THF (25 mL) were mixed. The reaction flask was then degassed by placing under vacuum followed by flushing with N$_2$ several times to prevent disulfide formation. After cooling to −78° C., triethylamine (1.85 mL, 13.3 mmol, 1 eq) was added via syringe and the flask degassed once more. The contents were allowed to warm to room temperature and the mixture was stirred overnight. TLC the following morning showed no malononitrile present, only thiol. Therefore, another 0.2 equivalents of malononitrile were added followed by degassing, followed by 0.5 equivalents of triethylamine, followed by degassing. TLC after a few hours no starting material was present. The reaction was worked up after stirring over the weekend at room temperature. The solvent was removed in vacuo and the residue was purified by flash chromatography on silica gel with 25–100% ethyl acetate in hexane. Two fractions were isolated. The faster eluting fraction yielded 1.63 g of a tan oily solid. The slower eluting fraction yielded 2.61 g of a tan oily solid. Both compounds were recrystallized from n-butylchloride. The faster eluting compound yielded 274 mg of a white solid (m.p. 147.0–148.0° C.). This compound proved to be the E isomer of the titled compound through NMR NOE experiments. The slower eluting compound yielded 1.85 g of a white solid (m.p. 130.0–130.5° C.). This compound proved to be the Z isomer of the titled compound through NMR NOE experiments. Anal. calcd. for C$_{16}$H$_{12}$F$_3$N$_3$S (faster eluting isomer): C, 57.31; H, 3.62; F, 17.00; N, 12.53; S, 9.56. Found: C, 57.19; H, 3.75; F, 16.83; N, 12.24; S, 9.50. Anal. calcd. for C$_{16}$H$_{12}$F$_3$N$_3$S (slower eluting isomer): C, 57.31; H, 3.62; F, 17.00; N, 12.53; S, 9.56. Found: C, 57.28; H, 3.80; F, 16.96; N, 12.37; S, 9.22. $^1$H-NMR (faster eluting isomer) (CDCl$_3$) δ7.75 (d, 1H, J=7 Hz); 7.57 (t, 1 H, J=7 Hz); 7.49 (t, 1H, J=7 Hz); 7.47 (d, 1H, J=7 Hz); 7.24 (d, 2H, J=7 Hz); 6.66 (d, 2H, J=7 Hz). $^1$H-NMR (slower eluting isomer) (CDCl$_3$) δ7.75 (d, 1H, J=7 Hz); 7.58 (t, 1 H, J=7 Hz); 7.48 (t, 1H, J=7 Hz); 7.43 (d, 1H, J=7 Hz); 7.40 (d, 2H, J=7 Hz); 6.68 (d, 2H, J=7 Hz).

Example 2

Z- and E-α-[amino[(2-aminophenyl)thio]methylene]-3-[(4-cyanophenyl)hydroxymethyl]benzeneacetonitrile

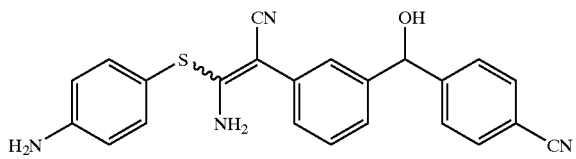

Part A. Preparation of 2-(3-bromophenyl)malononitrile

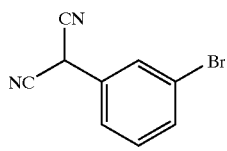

To a flame dried 5L 3-neck flask equipped with a mechamical overhead stirrer under nitrogen was added diisopropylamine (78.60 mL, 0.56 mol, 2.2 eq) and 2 L of benzene. After cooling to 0–5° C., 1.6 M n-BuLi (351.0 mL, 0.56 mol, 2.2 eq) was added dropwise via addition funnel while keeping the temperature at 0–5° C. The LDA was stirred for 45 min. at 0–5° C. 3-Bromophenylacetonitrile (50.0 g, 0.26 mol, 1.0 eq) dissolved in 200 mL of benzene was added dropwise via addition funnel keeping the temperature at 0–5° C. The mixture was stirred an additional 15 min at this temperature. 2-Chlorobenzylthiocyanate (*J. Am. Chem. Soc.,* 1954, 76, 585) (103.0 g, 0.56 mol, 2.2 eq) dissolved in 200 mL benzene was added dropwise via addition funnel keeping the temperature at 0–5° C. During the addition, a precipitate formed. The reaction was allowed to warm to room temperature and the mixture stirred overnight. The reaction was quenched by adding water and 200 mL 10% NaOH. The layers were separated, and the benzene layer extracted with 10% NaOH (3×1 L). The basic layers were collected and acidified with conc. HCl to pH 1–2. A precipitate formed. Methylene chloride was added to dissolve the precipitate. The layers were separated and the aqueous layer reextracted with methylene chloride (2×). The methylene chloride layers were collected, dried (MgSO$_4$) and the solvent removed in vacuo to yield 65.32 g of 2-(3-bromophenyl)malononitrile as a yellow solid. Recrystallization from methylcyclohexane yielded two crops: crop 1, 42.86 g of orange crystals, m.p. 99.5–101.5° C.; crop 2, 2.18 g of orange crystals, m.p. 97.0–99.0° C. Combined yield 79.9%. $^1$H-NMR (CDCl$_3$) δ: 7.67 (s, 1H); 7.63 (d, 1H, J=7 Hz); 7.47 (d, 1H, J=7 Hz); 7.39 (t, 1H, J=7 Hz); 5.08 (s, 1H).

Part B. Preparation of 2-[3-[(4-cyanophenyl)hydroxymethyl]phenyl]malononitrile

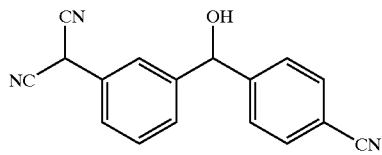

2-(3-Bromophenyl)malononitrile (the product from part A) (1.00 g, 4.52 mmol, 1 eq) was dissolved in dry THF (50 mL) under N$_2$ and cooled to −70° C. 1.6 M n-BuLi (5.94 mL, 9.50 mmol, 2.1 eq) was then added dropwise via syringe maintaining the temperature at −65 to −70° C. An orange slurry formed. The temperature was maintained for 20 min after which 4-cyanobenzaldehyde (0.59 g, 4.52 mmol, 1 eq) was added via syringe. After two hours, the reaction was complete. The reaction was added to water and the pH was adjusted to 3 with 1 N HCl. The mixture was extracted with ethyl acetate (3×), the organic layers combined, dried (MgSO$_4$) and the solvent removed in vacuo to yield 1.84 g an an amber oil. Flash chromatography on silica gel with 7:3 to 1:1 hexane/ethyl acetate yielded 2-(3-bromophenyl)malononitrile (0.88 g) as an amber oil. $^1$H-NMR (CDCl$_3$) δ: 7.66 (d, 2H, J=7 Hz); 7.60–7.15 (m, 6H); 5.95 (s, 1H); 5.07 (s, 1H); 2.63 (br s, 1H). NH$_4$-CI MS: 291 (M+NH$_4$)$^+$.

Part C. Preparation of Z- and E-α-[amino[(2-aminophenyl)thio]methylene]-3-[(4-cyanophenyl)hydroxymethyl]benzene-acetonitrile 2-[3-[(4-Cyanophenyl)hydroxymethyl]phenyl]malononitrile (the product from part B) (250 mg, 0.915 mmol, 1 eq), 2-aminothiophenol (0.10 mL, 0.915 mmol, 1 eq), triethylamine (0.13 mL, 0.915 mmol, 1 eq), and THF were reacted by the procedure described in Example 1, part B. After 4 hours, the solvent was then removed in vacuo and the residue purified by flash chromatography on silica gel with 1:1 hexane/ethyl acetate to yield the title compound (200 mg) as a mixture of isomers. HRMS calcd. for C$_{23}$H$_{18}$N$_4$OS: 399.1264; Found: 399.1280. $^1$H-NMR (CDCl$_3$) δ: (major isomer) 7.61 (d, 2H, J=7 Hz); 7.60–7.10 (m, 8H); 6.90–6.70 (m, 2H); 5.86 (br s, 1H); 4.71 (br s, 2H); 4.44 (br s, 2H); 2.51 (br s, 1H).

Example 3

Z- and E-α-[amino[(2-aminophenyl)thio]methylene]-3-[(4-pyridyl)hydroxymethyl]benzeneacetonitrile

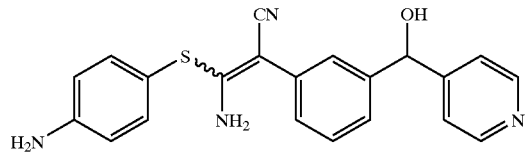

Part A. Preparation of 2-[3-[(4-pyridyl)hydroxymethyl]phenyl]malononitrile

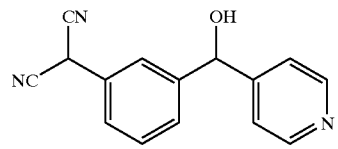

2-(3-Bromophenyl)malononitrile (the product from Example 2, part A) (2.00 g, 9.05 mmol, 1 eq) was dissolved in dry THF (100 mL) under N$_2$ and cooled to −70° C. 1.6 M n-BuLi (11.87 mL, 19.0 mmol, 2.1 eq) was then added dropwise via syringe maintaining the temperature at −65 to −70° C. An orange slurry formed. The temperature was maintained for 20 min after which 4-pyridinecarboxaldehyde (0.86 mL, 9.05 mmol, 1 eq) was added via syringe. After one hour, the reaction was essentially complete. It was worked up by adding water and adjusting the pH to 3 with 1 N HCl. The mixture was extracted with ethyl acetate (3×), the organic layers combined, dried (MgSO$_4$) and the solvent removed in vacuo to yield an an amber oil. Flash chromatography with 1:1 hexane/ethyl acetate to 100% ethyl acetate yielded 0.95 g of an orange glass as product. $^1$H-NMR (DMSO-$d_6$) δ: 8.41 (d, 2H, J=7 Hz); 7.26 (br s, 1H); 7.35–7.20 (m, 6H); 6.03 (br s, 1H); 5.65 (s, 1H).

Part B. Preparation of α-[amino[(2-aminophenyl)thio] methylene]-3-[(4-pyridyl)hydroxymethyl] benzeneacetonitrile 2-[3-[(4-Pyridyl)hydroxymethyl]phenyl]malononitrile (the product from Part A) (850 mg, 3.41 mmol, 1 eq), 2-aminothiophenol (0.36 mL, 3.41 mmol, 1 eq), triethylamine (0.48 mL, 3.41 mmol, 1 eq), and THF (20 mL) were reacted by the procedure described in Example 1, part B. As soon as the triethylamine was added, a precipitate began to form. More THF was added (50 mL) but the precipitate did not dissolve. The mixture was stirred overnight and the precipitate dissolved. TLC showed the reaction to be complete. The solvent was then removed in vacuo and the residue was purified by flash chromatography on silica gel with 1:1 hexane/ethyl acetate to 100% ethyl acetate to yield 950 mg of a white solid. The solid was stirred in THF and filtered to yield 462 mg of a white solid (mp 97.5–101.0° C.). NMR shows a mixture of isomers. An analytical sample was prepared by recrystallization (50 mg) from ethyl acetate. The recrystallized solids were filtered, rinsed with ether, and dried under high vacuum to yield 23 mg of a white solid (mp 150.0–151.0° C.). NMR showed the presence of mainly one isomer. Anal calcd. for $C_{21}H_{18}N_4OS \cdot 0.4\ H_2O$: C, 66.09; H, 4.96; N, 14.68; S, 8.40. Found: C, 66.16; H, 5.03; N, 14.46; S, 8.35. $^1$H-NMR (major isomer) (acetone-$d_6$) δ8.49 (d, 2H, J=7 Hz); 7.52 (s, 1H); 7.50–7.20 (m, 7H); 7.00–6.80 (m, 1H); 6.70 (t, 1H, J=7 Hz); 5.84 (d, 1H, J=6 Hz); 5.80–5.50 (m, 2H); 5.45–5.30 (m, 2H); 5.20 (d, 1H, J=6 Hz). The above procedure was repeated several times on larger scale to yield 112.12 g of the title compound. This material was stirred overnight at room temperature in 900 mL of ethyl acetate. The solids were filtered, rinsed with ether (1 L), and dried under high vacuum to yield 86.11 g of a white solid (mp 146.5–147.5° C.). Anal calcd. for $C_{21}H_{18}N_4OS$: C, 67.36; H, 4.86; N, 14.96; S, 8.56. Found: C, 67.39; H, 4.94; N, 14.76; S, 8.84.

Example 4

Z- and E-α-[amino[(2-aminophenyl)thio]methylene]-2-methyl-3-phenoxybenzeneacetonitrile

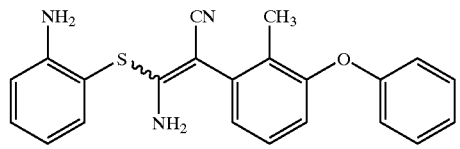

Part A. Preparation of 2,3-dimethyldiphenylether

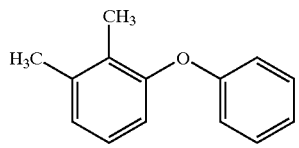

2,3-dimethylphenol (10 g, 82 mmol), sodium hydroxide (3.28 g, 82 mmol), water (1.8 mL) and chlorobenzene (70 mL) were refluxed for 3 h under nitrogen in a flask equipped with a Dean-Stark trap. Water and chlorobenzene removed from the trap several times (100 mL total) while adding an equal volume of chlorobenzene to the flask. The resulting suspension was dried further by refluxing through a soxhlet extractor filled with 3A molecular sieves for 30 min. Cuprous iodide (0.81 g, 0.082 mmol) and tris[2-(2-methoxyethoxy)ethyl]amine (1.5 mL, 4.1 mmol) were added and the reaction was refluxed overnight. The solution was decanted from the solid. Additional cuprous iodide (0.81 g, 0.082 mmol) and tris[2-(2-methoxyethoxy)ethyl]amine (1.5 mL, 4.1 mmol) were added to the solution and the reaction was refluxed overnight with mechanical stirring. The reaction mixture was absorbed onto silica gel and eluted with hexane to afford the title compound (1.4 g). GC-MS: Calcd, 199; Found, 199. $^1$H-NMR (CDCl$_3$) δ: 7.28 (t, 2H); 7.04 (m, 3H); 6.88 (d, 2H); 6.78 (d, 1H); 2.32 (s, 3H); 2.25 (s, 3H).

Part B. Preparation of 2-(3-phenoxy-2-methylphenyl)malononitrile

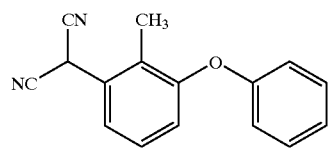

A solution of 2,3-dimethyldiphenylether (2.2 g, 11 mol), N-bromosuccinimide (1.76 g, 11 mmol) and benzoyl peroxide (0.27 g, 1 mmol) in carbon tetrachloride (60 mL) was refluxed for 2.5 h. The reaction mixture was added to methylene chloride and extracted with saturated aqueous sodium bisulfite, water (twice), and brine. The organic layer was dried over sodium sulfate and the residue was purified by chromatography on silica gel with hexane to afford a mixture 3-bromomethyl-2-methyldiphenylether and 2-bromomethyl-3-methyldiphenylether (2.0 g).

A solution of the above bromination products (2.0 g, 7.2 mmol) and tetraethylammonium cyanide (1.2 g, 7.7 mmol) in dichloromethane (60 mL) was refluxed for 1 h. The reaction was added to dichloromethane and extracted with 10% aqueous sodium hydroxide (three times) and brine (twice). After concentrating the organic layer, the residue was purified by chromatography on silica gel with toluene and 5% ethyl acetate in toluene to afford a 1:3 mixture of 2-(3-phenoxy-2-methylphenyl)acetonitrile and 2-(2-phenoxy-6-methylphenyl)acetonitrile (1.08 g). $^1$H-NMR (CDCl$_3$) δ: 6.7–7.2 (m, 8H); 3.78 (s, 1.5H); 3.74(s, 0.5H); 2.48 (s, 2.25H); 2.28(s, 0.75H).

Methyllithium (4.3 mL of a 2.5 M solution, 10.7 mmol) was added to a solution of diisopropylamine (1.5 mL, 10.7 mmole) in dry benzene (70 mL) cooled in an ice-water bath. After stirring for 1 h, a solution of the above mixture of phenylacetonitriles in dry benzene (30 mL) was added dropwise. After stirring for 1 h at 0° C., a solution of 2-chlorobenzylthiocyanate in dry benzene was added. After stirring for 1 h while the reaction mixture warmed to room temperature, the reaction mixture was added to benzene and extracted with 10% aqueous sodium hydroxide (4x). The combined aqueous layers were acidified to pH 1 with concentrated hydrochloric acid and extracted with ethyl acetate. The organic layer was dried over sodium sulfate, concentrated, and purified twice by silica gel chromatography with 0–10% ethyl acetate in toluene and then 10% ether in hexane, removing the high Rf major isomer and affording isomerically pure title compound (61 mg) as a pale yellow solid. $^1$NMR(CDCl$_3$) δ: 7.2–7.4 (m, 4H); 7.13 (t, 1H); 6.9–7.0 (m, 3H); 5.10 (s, 1H); 2.40 (s, 3H). HRMS: Calculated for $C_{16}H_{12}N_2O$ (M): 248.0959; Found: 248.0950.

Part C. Preparation of Z- and E-α-[amino[(2-aminophenyl)thio]methylene]-2-methyl-3-phenoxybenzeneacetonitrile A solution of 2-(3-phenoxy-2-methylphenyl) malononitrile (50 mg, 0.20 mmol), 2-aminothiophenol (21 uL, 0.20 mmol) and triethylamine (28 uL) in tetrahydrofuran was stirred under nitrogen overnight. The reaction was added to water and extracted with ethyl acetate. The combined organic layers were washed with brine, dried over sodium sulfate, and concentrated. The residue was purified by chromatography on silica gel with 20–50% ether in hexanes to afford the title compound as a colorless oil (30 mg). $^1$H-NMR (CDCl$_3$) was consistent with the presence of a 1:1 mixture of isomers. δ: 7.49 (d, 0.5H); 6.7–7.4 (m, 11.5H); 4.83 (br s, 1H); 4.51 (br s, 1H); 4.41 (br s, 1H); 4.33 (br s, 1H); 2.31 (s, 1.5H); 2.25 (s, 1.5H). HRMS: Calculated for $C_{22}H_{20}N_3OS$ (M+H): 374.1327; Found: 374.1307.

Example 5

Z- and E-α-[amino[(2-aminophenyl)thio] methylene]-4-chloro-β-(2-methylphenyl) benzenepropanenitrile

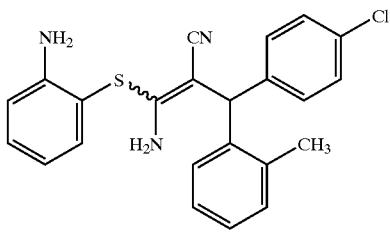

Part A. Preparation of 2-(2-methylbenzylidene) malononitrile

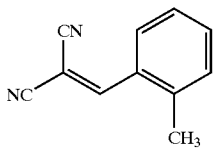

A solution of 2-methylbenzaldehyde (9.6 mL, 83 mmol), malononitrile (5.5 g, 83 mmol) and 3.5 M ammonium acetate in acetic acid (2.4 mL, 8.4 mmol) in isopropanol (83 mL) was stirred overnight at room temperature. A precipitate formed. Water (100 mL) was added and the precipitate was collected. The precipitate was washed with water (50 mL) and vacuum dried to afford of 2-(2-methylbenzylidene) malononitrile (12.7 g) as a white solid (mp 105–106°). $^1$H-NMR (CDCl$_3$) δ: 8.10 (s 1H); 8.08 (d, 1H); 7.50 (dd, 1H); 7.30–7.40 (m, 2H); 2,45 (s, 3H).

Part B. Preparation of 2-[α-(2-methylphenyl)-4-chlorobenzyl]malononitrile

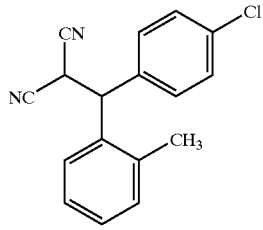

4-Chlorophenylmagnesium bromide (2.1 mL of a 1.0 M solution in ether, 2.1 mmol) was added dropwise to a solution of 2-(2-methylbenzylidene)malononitrile (0.32 g, 1.9 mmol) in dry tetrahydrofuran (7.5 mL) at 0° C. and stirred for 1 h. Saturated aqueous ammonium chloride was added and the layers were separated. The aqueous layer was extracted twice with dichloromethane and the combined organics layers were dried over magnesium sulfate. After concentrating, the residue was purified by flash chromatography on silica gel with 12.5% ethyl acetate in hexanes to afford the title compound (0.25 g) as a white solid (mp 132–140°). $^1$H-NMR (CDCl$_3$): δ: 7.20–7.39 (m 8H); 4.78 (d, 1H); 2.25 (s, 3H). GC-MS: m/e=281/283 (M+H).

Part C. Preparation of Z- and E-α-[amino[(2-aminophenyl) thio]methylene]-4-chloro-β-(2-methylphenyl) benzenepropanenitrile A solution of 2-[α-(2-methylphenyl)-4-chlorobenzyl] malononitrile (0.20 g, 0.71 mmol), 2-aminothiophenol (0.11 mL, 1.00 mmol) and triethylamine (0.14 mL, 1.00 mmol) in tetrahydrofuran (1.4 mL) was stirred under nitrogen for 78 h. The reaction mixture was absorbed onto silica gel and eluted with 20–30% ethyl acetate in hexanes to afford the title compound (253 mg) as a white foam (mp 63.5–72°). $^1$H-NMR (CDCl$_3$) was consistent with the presence of a 4:6 mixture of isomers: δ7.44 (d, 0.4H); 7.10–7.36 (m, 9.6H); 6.71–6.79 (m, 2H); 5.34 (s, 0.6H); 4.97 (s, 0.4H); 4.65 (br s, 1.2H); 4.44 (br s, 0.8H); 4.12 (br s, 2H); 2.33 (s, 1.8H); 2.22 (s, 1.2H). HRMS: Calcd for $C_{23}H_{21}N_3SCl$ (M+H), 406.1145; Found, 406.1130. Elem. Anal. Calcd for $C_{23}H_{20}N_3SCl$: C, 68.05; H, 4.98; N, 10.35; S, 7.91. Found: C, 68.03; H, 5.09; N, 10.20; S, 7.97.

Examples 6–51

The following compounds were prepared by procedures similar to those described above.

| Ex. | Name |
| --- | --- |
| 6 | Z- and E-α-[amino[(2-aminophenyl)thio]methylene]-4-chloro-2-methyl-β-phenylbenzenepropanenitrile |
| 7 | Z- and E-α-[amino[(2-aminophenyl)thio]methylene]-3-[(2,4-dinitrophenyl)hydroxymethyl]benzeneacetonitrile |
| 8 | Z- and E-α-[amino[(2-aminophenyl)thio]methylene]-3-[(4-carbomethoxyphenyl)hydroxymethyl]benzeneacetonitrile |
| 9 | Z- and E-α-[amino[(2-aminophenyl)thio]methylene]-3-[(4-nitrophenyl)hydroxymethyl]benzeneacetonitrile |
| 10 | Z- and E-α-[amino[(2-aminophenyl)thio]methylene]-3-[(pentafluorophenyl)hydroxymethyl]benzeneacetonitrile |
| 11 | Z- and E-α-[amino[(2-aminophenyl)thio]methylene]-2-methyl-3-[(4-pyridyl)hydroxymethyl]benzeneacetonitrile |
| 12 | Z- and E-α-[amino[(2-aminophenyl)thio]methylene]-2-methyl-3-[(phenyl)hydroxymethyl]benzeneacetonitrile |
| 13 | Z- and E-α-[amino[(2-aminophenyl)thio]methylene]-2-methyl-3-[(4-pyridyl)hydroxymethyl]benzeneacetonitrile |
| 14 | Z- and E-α-[amino[(2-hydroxyphenyl)thio]methylene]-3-[(4-cyanophenyl)hydroxymethyl]benzeneacetonitrile |
| 15 | Z- and E-α-[amino[(2-aminophenyl)thio]methylene]-3-[(3-nitrophenyl)hydroxymethyl]benzeneacetonitrile |
| 16 | Z- and E-α-[amino[(2-aminophenyl)thio]methylene]-2-methyl-3-[(pentafluorophenyl)hydroxymethyl]benzeneacetonitrile |
| 17 | Z- and E-α-[amino[(2-hydroxyphenyl)thio]methylene]-3-[(4-pyridyl)hydroxymethyl]benzeneacetonitrile |
| 18 | Z- and E-α-[amino[(2-aminophenyl)thio]methylene]-3-[(2-trifluoromethylphenyl)hydroxymethyl]benzeneacetonitrile |
| 19 | Z- and E-α-[amino[(4-aminophenyl)thio]methylene]-3-[(4-pyridyl)hydroxymethyl]benzeneacetonitrile |
| 20 | Z- and E-α-[amino[(4-hydroxyphenyl)thio]methylene]-3-[(4-pyridyl)hydroxymethyl]benzeneacetonitrile |
| 21 | Z- and E-α-[amino[(2-aminophenyl)thio]methylene]-3-[(3-cyanophenyl)hydroxymethyl]benzeneacetonitrile |
| 22 | Z- and E-α-[amino[(4-aminophenyl)thio]methylene]-3-[(4-cyanophenyl)hydroxymethyl]benzeneacetonitrile |
| 23 | Z- and E-α-[amino(phenylthio)methylene]-3-[(4-cyanophenyl)hydroxymethyl]benzeneacetonitrile |

-continued

| Ex. | Name |
|---|---|
| 24 | Z- and E-α-[amino(phenylthio)methylene]-3-[(4-pyridyl)hydroxymethyl]benzeneacetonitrile |
| 25 | Z- and E-α-[amino[(4-aminophenyl)thio]methylene]-2-bromobenzeneacetonitrile |
| 26 | Z- and E-α-[amino[(2-aminophenyl)thio]methylene]-3-[(2,4-dimethylphenyl)hydroxymethyl]benzeneacetonitrile |
| 27 | Z- and E-α-[amino[(2-aminophenyl)thio]methylene]-3-[(phenyl)hydroxymethyl]benzeneacetonitrile |
| 28 | Z- and E-α-[amino[(2-aminophenyl)thio]methylene]-3-[(2-thienyl)hydroxymethyl]benzeneacetonitrile |
| 29 | Z- and E-α-[amino[(2-aminophenyl)thio]methylene]-4-chloro-β-phenylbenzenepropanenitrile |
| 30 | Z- and E-α-[amino[(2-thienyl)thio]methylene]-3-[(phenyl)hydroxymethyl]benzeneacetonitrile |
| 31 | Z- and E-α-[amino[(2,4-diaminophenyl)thio]methylene]-1-naphthyleneacetonitrile |
| 32 | Z- and E-α-[amino[(2-aminophenyl)thio]methylene]-2-methyl-β-(4-pyridyl)benzenepropanenitrile |
| 33 | Z- and E-α-[amino[(4-aminophenyl)thio]methylene]-3-(benzyl)benzeneacetonitrile |
| 34 | Z- and E-α-[amino[(2-naphthyl)thio]methylene]-1-naphthyleneacetonitrile |
| 35 | Z- and E-α-[amino[(2-aminophenyl)thio]methylene]-3-(benzoyl)benzeneacetonitrile |
| 36 | Z- and E-α-[amino[(2-aminophenyl)thio]methylene]-β-(1-methyl-2-pyrrolyl)benzenepropanenitrile |
| 37 | Z- and E-α-[amino[(2-aminophenyl)thio]methylene]-3-phenoxybenzeneacetonitrile |
| 38 | Z- and E-α-[amino[(2-aminophenyl)thio]methylene]-2-bromobenzeneacetonitrile |
| 39 | Z- and E-α-[amino[(2-aminophenyl)thio]methylene]-3-[(2-furanyl)hydroxymethyl]benzeneacetonitrile |
| 40 | Z- and E-α-[amino[(2-thienyl)thio]methylene]-3-[(2,3,4,5,6-pentafluorophenyl)hydroxymethyl]benzeneacetonitrile |
| 41 | Z- and E-α-[amino[(2-aminophenyl)thio]methylene]-3-[(3-methyl-2-pyridyl)hydroxymethyl]benzeneacetonitrile |
| 42 | Z- and E-α-[amino[(4-aminophenyl)thio]methylene]-2-methylbenzeneacetonitrile |
| 43 | Z- and E-α-[amino[(4-aminophenyl)thio]methylene]-4-(1,1-dimethylethyl)benzeneacetonitrile |
| 44 | Z- and E-α-[amino[(4-aminophenyl)thio]methylene]-1-naphthyleneacetonitrile |
| 45 | Z- and E-α-[amino[(2-aminophenyl)thio]methylene]-3-(trifluoromethyl)benzeneacetonitrile |
| 46 | Z- and E-α-[amino[(2-aminophenyl)thio]methylene]-1-naphthyleneacetonitrile |
| 47 | Z- and E-α-[amino[(2-aminophenyl)thio]methylene]-2-(trifluoromethyl)benzeneacetonitrile |
| 48 | Z- and E-α-[amino[(4-aminophenyl)thio]methylene]-4-methylbenzeneacetonitrile |
| 49 | Z- and E-α-[amino[(2-aminophenyl)thio]methylene]-2-methylbenzeneacetonitrile |
| 50 | Z- and E-α-[amino[(2-fluorophenyl)thio]methylene]-1-naphthyleneacetonitrile |
| 51 | Z- and E-α-[amino[(2-aminophenyl)thio]methylene]-3-phenylbenzeneacetonitrile |

| Example | FORMULA | HRMS Calculated* | HRMS Found* |
|---|---|---|---|
| 6 | C23H20C1N3S | 406.1145 | 406.1148 |
| 7 | C22H17N5O5S | 464.1029 | 464.1024 |
| 8 | C24H21N3O3S | 432.1382 | 432.1364 |
| 9 | C22H18N4O3S | 419.1178 | 419.1168 |
| 10 | C22H14F5N3OS | 464.0856 | 464.0827 |
| 11 | C22H20N4OS | 389.1436 | 389.1428 |
| 12 | C23H21N3OS | 388.1484 | 388.1471 |
| 13 | C22H20N4OS | 388.1436 | 388.1436 |
| 14 | C23H17N3O2S | 400.1120 | 400.1105 |
| 15 | C22H18N4O3S | 419.1179 | 419.1156 |
| 16 | C23H16F5N3OS | 478.1013 | 478.1002 |
| 17 | C21H18N4OS | 376.1120 | 376.1103 |
| 18 | C23H18F3N3OS | 442.1201 | 442.1200 |
| 19 | C21H18N4OS | 375.1280 | 375.1268 |
| 20 | C21H17N3OS | 376.1120 | 376.1104 |
| 21 | C23H18N4OS | 399.1280 | 399.1273 |
| 22 | C23H18N4OS | 399.1280 | 399.1265 |
| 24 | C21H17N3OS | 360.1171 | 360.1172 |
| 25 | C15H12BrN3S | 360.1171 | 360.1172 |
| 26 | C24H23N3OS | 402.1640 | 402.1648 |
| 27 | C22H19N3OS | 374.1327 | 374.1327 |
| 28 | C20H17N3OS2 | 379.0813 (M+) | 379.0799 (M+) |
| 29 | C22H18C1N3S | 392.0988 | 392.0982 |
| 30 | C20H16N2OS2 | 365.0782 | 365.0763 |
| 31 | C19H16N4S | 333.1174 | 333.1166 |
| 32 | C22H20N4S | 373.1496 | 373.1487 |
| 33 | C22H19N3S | 358.1378 | 358.1393 |
| 34 | C23H17N3S | 368.1221 | 368.1227 |
| 35 | C22H17N3OS | 372.1171 | 372.1160 |
| 36 | C21H20N4S | 361.1487 | 361.1479 |
| 37 | C21H17N3OS | 360.1171 | 360.1144 |
| 39 | C20H17N3O2S | 364.1120 | 364.1097 |
| 40 | C20H11F5N2OS2 | 455.0311 | 455.0305 |
| 41 | C22H20N4OS | 389.1436 | 389.1431 |
| 43 | C19H21N3S | 324.1534 | 324.1524 |
| 44 | C19H15N3S | 318.1065 | 318.1076 |
| 45 | C16H12F3N3S | 336.0782 | 336.0782 |
| 46 | C19H15N3S | 318.7065 | 318.1048 |
| 47 | C16H12F3N3S | 336.0782 | 336.0776 |
| 51 | C21H17N3S | 344.1221 | 334.1208 |

*Calculated for M + H unless noted.

| Example | Solvent | Chemical Shift |
|---|---|---|
| 23 | CDC13 | 7.15–7.65 (m, 13H); 5.85&2.88 (2 d, 1H); 4.61&4.88 (2 br s, 2H); 2.50&2.59 (2 d, 2H). |
| 25 | CDC13 | 6.64–7.68 (m, 8H); 3.95–4.81 (3 br s, 4H). |
| 38 | CDC13 | 6.54–7.71 (m, 8H); 4.37–4.90 (4 br s, 4H). |
| 42 | CDC13 | 6.56–7.43 (m, 8H); 3.75–4.70 (4 br s, 4H); 2.37&2.40 (2 s, 3H). |
| 48 | CDC13 | 6.57–7.41 (m, 8H); 3.75–4.74 (4 br s, 4H); 2.33&2.34 (2 s, 3H). |
| 49 | CDC13 | 6.72–7.54 (m, 8H); 4.26–4.80 (3 br s, 4H); 2.36&2.43 (2 s, 3H). |

Utility

Compounds of the present invention are inhibitors of the dual-specificity kinase MEK1/MEK2 (Mapk or Erk kinase, where Mapk=mitogen-activated protein kinase) and are expected to be useful for treating proliferative diseases, e.g. cancer, psoriasis, restenosis or atherosclerosis, and also autoimmune diseases. The presently claimed MEK inhibitors are also expected to have utility as radiosensitizers for the treatment of solid tumors. In addition, the presently claimed compounds are expected to have utility for the treatment of chronic pain or for inhibiting memory acquisition. Assays for chronic pain are found Science and Medicine (1996), Nov./Dec., 22–31. Assays for mammalian associative learning are found in Nature Neuroscience (1998) 1 (1) 602–609.

The ERK signal transduction pathway includes two very similar forms of MEK, MEK1 and MEK2, and two similar forms of ERK, ERK1 and ERK2. To block signal transduction via the ERK pathway, a MEK inhibitor must prevent ERK1 and/or ERK2 from being phosphorylated (and thereby activated) by the kinases MEK1 or MEK2. The different roles played by MEK1 and MEK2 and by ERK1 and ERK2 are not currently understood well understood and they may be redundant under some or all circumstances. MEK1 and MEK2 are phosphorylated (and thereby activated) by an upstream kinase, RAF. Since MEK1 or MEK2 have little ability to phosphorylate ERK1 and ERK2 until they have been phosphorylated and since they are usually isolated in their unphosphorylated state, it is difficult to obtain adequate quantities of phosphorylated MEK1 or MEK2 suitable for assaying many compounds. To make assays more practical, a constitutively active mutant of MEK1 (e.g., 2X-MEK1)(see *J. Biol. Chem.* (1998) 29, 18623–18632) was initially used to characterize the MEK inhibitors of this invention. This mutant enzyme has negatively-charged residues at the residues which are normally phosphorylated by RAF. Selected inhibitors of 2X-MEK1 disclosed herein have been shown to be inhibitors of phosphorylated (i.e., active) wild-type MEK1 and MEK2. Furthermore, many of the MEK inhibitors of this invention have been shown to be capable of blocking phosphorylation of ERK induced by treatment of Jurkat cells with TPA (see *J. Biol. Chem.* (1998) 29, 18623–18632).

Selected MEK inhibitors from this invention have also been shown to block the upregulation of AP-1 expression in Cos-7 cells induced by stimulation with TPA (see *J. Biol. Chem.* (1998) 29, 18623–18632). AP-1 in turn regulates the expression of a number of pro-inflammatory and growth-stimulating genes including. These experiments prove that inhibitors of 2X-MEK1 function as inhibitors of MEK and ERK signal transduction in cell culture.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as ethanol, glycerol, and water. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrators include, without limitation, starch, methyl cellulose, agar, bentonite, and xanthan gum.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:
1. A compound of formula Ia or Ib:

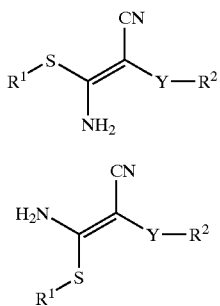

or stereoisomer or pharmaceutically acceptable salt form thereof, wherein;

$R^1$ is phenyl or naphthyl, and $R^1$ is substituted with 0–2 $R^a$;

$R^a$ is selected from H, Cl, F, Br, I, $C_{1-4}$ alkyl, $C_{1-4}$ alkoxy, OH, $CH_2OH$, $NH_2$, ($C_{1-3}$ alkyl)NH, ($C_{1-3}$ alkyl)$_2$N, ($H_2NCH_2C(O)$)NH, ($H_2NCH(CH_3)C(O)$)NH, ($CH_3NHCH_2C(O)$)NH, (($CH_3)_2NCH_2C(O)$)NH, $CF_3$, $OCF_3$, —CN, $NO_2$, $C(O)NH_2$, and $CH_3C(O)NH$;

Y is selected from phenyl substituted with 0–5 $R^b$, naphthyl substituted with 0–5 $R^b$, and $CHR^3$;

$R^b$ is selected from H, Cl, F, Br, I, $C_{1-4}$ alkyl, OH, $C_{1-4}$ alkoxy, $CH_2OH$, $CH(OH)CH_3$, $CF_3$, $OCF_3$, —CN, $NO_2$, $NH_2$, ($C_{1-3}$ alkyl)NH, ($C_{1-3}$ alkyl)$_2$N, and $C(O)O$—$C_{1-4}$ alkoxy;

$R^2$ is selected from H, $R^{2a}$, $C(O)R^{2a}$, $CH(OH)R^{2a}$, $CH_2R^{2a}$, $OR^{2a}$, $SR^{2a}$, and $NHR^{2a}$;

$R^{2a}$ is selected from phenyl, and naphthyl, and $R^{2a}$ is substituted with 0–5 $R^b$;

$R^3$ is phenyl substituted with 0–2 $R^c$ or naphthyl substituted with 0–2 $R^c$; and, $R^c$ is selected from H, Cl, F, Br, I, $C_{1-4}$ alkyl, OH, $C_{1-4}$ alkoxy, $CH_2OH$, $CH(OH)CH_3$, $CF_3$, $OCF_3$, —CN, $NO_2$, $NH_2$, ($C_{1-3}$ alkyl)NH, ($C_{1-3}$ alkyl)$_2$N, and $C(O)O$—$C_{1-4}$ alkoxy.

2. A compound of claim 1, wherein:

$R^1$ is phenyl, and $R^1$ is substituted with 0–2 $R^a$;

$R^a$ is selected from H, Cl, F, $C_{1-4}$ alkyl, $C_{1-4}$ alkoxy, OH, $CH_2OH$, $NH_2$, ($C_{1-3}$ alkyl)NH, ($C_{1-3}$ alkyl)$_2$N, ($H_2NCH_2C(O)$)NH, ($H_2NCH(CH_3)C(O)$)NH, ($CH_3NHCH_2C(O)$)NH, (($CH_3)_2NCH_2C(O)$)NH, and $CH_3C(O)NH$;

Y is selected from phenyl substituted with 0–5 $R^b$, naphthyl substituted with 0–5 $R^b$, and $CHR^3$;

$R^b$ is selected from H, Cl, F, Br, $C_{1-4}$ alkyl, OH, $C_{1-4}$ alkoxy, $CH_2OH$, $CH(OH)CH_3$, $CF_3$, —CN, $NO_2$, $NH_2$, and ($C_{1-3}$ alkyl)NH, ($C_{1-3}$ alkyl)$_2$N;

$R^2$ is selected from H, $R^{2a}$, $C(O)R^{2a}$, $CH(OH)R^{2a}$, $CH_2R^{2a}$, and $OR^{2a}$;

$R^{2a}$ is selected from phenyl, and naphthyl, and $R^{2a}$ is substituted with 0–5 $R^b$;

$R^3$ is phenyl substituted with 0–2 $R^c$ or naphthyl substituted with 0–2 $R^c$; and, $R^c$ is selected from H, Cl, F, Br, I, $C_{1-4}$ alkyl, OH, $C_{1-4}$ alkoxy, $CH_2OH$, $CH(OH)CH_3$, $CF_3$, —CN, $NO_2$, $NH_2$, ($C_{1-3}$ alkyl)NH, and ($C_{1-3}$ alkyl)$_2$N.

3. A compound according to claim 2, wherein:

$R^1$ is phenyl, and $R^1$ is substituted with 0–2 $R^a$;

$R^a$ is selected from H, OH, and $NH_2$;

Y is selected from phenyl substituted with 0–2 $R^b$, naphthyl substituted with 0–2 $R^b$, and $CHR^3$;

$R^b$ is selected from H, Cl, F, Br, $C_{1-4}$ alkyl, OH, $C_{1-4}$ alkoxy, $CH_2OH$, $CH(OH)CH_3$, $CF_3$, —CN, $NO_2$, $NH_2$, and ($C_{1-3}$ alkyl)NH, ($C_{1-3}$ alkyl)$_2$N;

$R^2$ is selected from H, $R^{2a}$, $C(O)R^{2a}$, $CH(OH)R^{2a}$, $CH_2R^{2a}$, and $OR^{2a}$;

$R^{2a}$ is selected from phenyl, and naphthyl, and $R^{2a}$ is substituted with 0–5 $R^b$;

$R^3$ is phenyl substituted with 0–2 $R^c$ or naphthyl substituted with 0–2 $R^c$; and, $R^c$ is selected from H, Cl, F, Br, I, $C_{1-4}$ alkyl, OH, $C_{1-4}$ alkoxy, $CH_2OH$, $CH(OH)CH_3$, $CF_3$, —CN, $NO_2$, $NH_2$, ($C_{1-3}$ alkyl)NH, and ($C_{1-3}$ alkyl)$_2$N.

4. A compound according to claim 1, wherein the compound is selected from:

E- and Z-α-[amino[(2-aminophenyl)thio]methylene]-3-[(2,4-dinitrophenyl)hydroxymethyl]benzeneacetonitrile;

E- and Z-α-[amino[(2-aminophenyl)thio]methylene]-3-[(4-carbomethoxyphenyl)hydroxymethyl]benzeneacetonitrile;

E- and Z-α-[amino[(2-aminophenyl)thio]methylene]-3-[(4-nitrophenyl)hydroxymethyl]benzeneacetonitrile;

E- and Z-α-[amino[(2-aminophenyl)thio]methylene]-3-[(pentafluorophenyl)hydroxymethyl]benzeneacetonitrile;

E- and Z-α-[amino[(2-aminophenyl)thio]methylene]-2-methyl-3-[(phenyl)hydroxymethyl]benzeneacetonitrile;

E- and Z-α-[amino[(2-hydroxyphenyl)thio]methylene]-3-[(4-cyanophenyl)hydroxymethyl]benzeneacetonitrile;

E- and Z-α-[amino[(2-aminophenyl)thio]methylene]-3-[(3-nitrophenyl)hydroxymethyl]benzeneacetonitrile;

E- and Z-α-[amino[(2-aminophenyl)thio]methylene]-2-methyl-3-[(pentafluorophenyl)hydroxymethyl]benzeneacetonitrile;

E- and Z-α-[amino[(2-aminophenyl)thio]methylene]-3-[(2-trifluoromethylphenyl)hydroxymethyl]benzeneacetonitrile;

E- and Z-α-[amino[(2-aminophenyl)thio]methylene]-3-[(3-cyanophenyl)hydroxymethyl]benzeneacetonitrile;

E- and Z-α-[amino[(4-aminophenyl)thio]methylene]-3-[(4-cyanophenyl)hydroxymethyl]benzeneacetonitrile;

E- and Z-α-[amino(phenylthio)methylene]-3-[(4-cyanophenyl)hydroxymethyl]benzeneacetonitrile;

E- and Z-α-[amino[(4-aminophenyl)thio]methylene]-2-bromobenzeneacetonitrile;

E- and Z-α-[amino[(2-aminophenyl)thio]methylene]-3-[(2,4-dimethylphenyl)hydroxymethyl]benzeneacetonitrile;

E- and Z-α-[amino[(2-aminophenyl)thio]methylene]-3-[(phenyl)hydroxymethyl]benzeneacetonitrile;

E- and Z-α-[amino[(2-thienyl)thio]methylene]-3-[(phenyl)hydroxymethyl]benzeneacetonitrile;

E- and Z-α-[amino[(2,4-diaminophenyl)thio]methylene]-1-naphthyleneacetonitrile;

E- and Z-α-[amino[(4-aminophenyl)thio]methylene]-3-(benzyl)benzeneacetonitrile;

E- and Z-α-[amino[(2-naphthyl)thio]methylene]-1-naphthyleneacetonitrile;

E- and Z-α-[amino[(2-aminophenyl)thio]methylene]-3-(benzoyl)benzeneacetonitrile;

E- and Z-α-[amino[(2-aminophenyl)thio]methylene]-3-phenoxybenzeneacetonitrile;

E- and Z-α-[amino[(2-aminophenyl)thio]methylene]-2-bromobenzeneacetonitrile;

E- and Z-α-[amino[(2-thienyl)thio]methylene]-3-[(2,3,4,5,6-pentafluorophenyl)hydroxymethyl]benzeneacetonitrile;

E- and Z-α-[amino[(4-aminophenyl)thio]methylene]-2-methylbenzeneacetonitrile;

E- and Z-α-[amino[(4-aminophenyl)thio]methylene]-4-(1,1-dimethylethyl)benzeneacetonitrile;

E- and Z-α-[amino[(4-aminophenyl)thio]methylene]-1-naphthyleneacetonitrile;

E- and Z-α-[amino[(2-aminophenyl)thio]methylene]-3-(trifluoromethyl)benzeneacetonitrile;

E- and Z-α-[amino[(2-aminophenyl)thio]methylene]-1-naphthyleneacetonitrile;

E- and Z-α-[amino[(2-aminophenyl)thio]methylene]-2-(trifluoromethyl)benzeneacetonitrile;

E- and Z-α-[amino[(4-aminophenyl)thio]methylene]-4-methylbenzeneacetonitrile;

E- and Z-α-[amino[(2-aminophenyl)thio]methylene]-2-methylbenzeneacetonitrile;

E- and Z-α-[amino[(2-fluorophenyl)thio]methylene]-1-naphthyleneacetonitrile; and, E- and Z-α-[amino[(2-aminophenyl)thio]methylene]-3-phenyl benzeneacetonitrile;

or a pharmaceutically acceptable salt form thereof.

5. A compound according to claim 1, wherein the compound is selected from:

E-α-[amino[(2-aminophenyl)thio]methylene]-3-[(2,4-dinitrophenyl)hydroxymethyl]benzeneacetonitrile;

E-α-[amino[(2-aminophenyl)thio]methylene]-3-[(4-carbomethoxyphenyl)hydroxymethyl]benzeneacetonitrile;

E-α-[amino[(2-aminophenyl)thio]methylene]-3-[(4-nitrophenyl)hydroxymethyl]benzeneacetonitrile;

E-α-[amino[(2-aminophenyl)thio]methylene]-3-[(pentafluorophenyl)hydroxymethyl]benzeneacetonitrile;

E-α-[amino[(2-aminophenyl)thio]methylene]-2-methyl-3-[(phenyl)hydroxymethyl]benzeneacetonitrile;

E-α-[amino[(2-hydroxyphenyl)thio]methylene]-3-[(4-cyanophenyl)hydroxymethyl]benzeneacetonitrile;

E-α-[amino[(2-aminophenyl)thio]methylene]-3-[(3-nitrophenyl)hydroxymethyl]benzeneacetonitrile;

E-α-[amino[(2-aminophenyl)thio]methylene]-2-methyl-3-[(pentafluorophenyl)hydroxymethyl]benzeneacetonitrile;

E-α-[amino[(2-aminophenyl)thio]methylene]-3-[(2-trifluoromethylphenyl)hydroxymethyl]benzeneacetonitrile;

E-α-[amino[(2-aminophenyl)thio]methylene]-3-[(3-cyanophenyl)hydroxymethyl]benzeneacetonitrile;

E-α-[amino[(4-aminophenyl)thio]methylene]-3-[(4-cyanophenyl)hydroxymethyl]benzeneacetonitrile;

E-α-[amino(phenylthio)methylene]-3-[(4-cyanophenyl)hydroxymethyl]benzeneacetonitrile;

E-α-[amino[(4-aminophenyl)thio]methylene]-2-bromobenzeneacetonitrile;

E-α-[amino[(2-aminophenyl)thio]methylene]-3-[(2,4-dimethylphenyl)hydroxymethyl]benzeneacetonitrile;

E-α-[amino[(2-aminophenyl)thio]methylene]-3-[(phenyl)hydroxymethyl]benzeneacetonitrile;

E-α-[amino[(2-thienyl)thio]methylene]-3-[(phenyl)hydroxymethyl]benzeneacetonitrile;

E-α-[amino[(2,4-diaminophenyl)thio]methylene]-1-naphthyleneacetonitrile;

E-α-[amino[(4-aminophenyl)thio]methylene]-3-(benzyl)benzeneacetonitrile;

E-α-[amino[(2-naphthyl)thio]methylene]-1-naphthyleneacetonitrile;

E-α-[amino[(2-aminophenyl)thio]methylene]-3-(benzoyl)benzeneacetonitrile;

E-α-[amino[(2-aminophenyl)thio]methylene]-3-phenoxybenzeneacetonitrile;

E-α-[amino[(2-aminophenyl)thio]methylene]-2-bromobenzeneacetonitrile;

E-α-[amino[(2-thienyl)thio]methylene]-3-[(2,3,4,5,6-pentafluorophenyl)hydroxymethyl]benzeneacetonitrile;

E-α-[amino[(4-aminophenyl)thio]methylene]-2-methylbenzeneacetonitrile;

E-α-[amino[(4-aminophenyl)thio]methylene]-4-(1,1-dimethylethyl)benzeneacetonitrile;

E-α-[amino[(4-aminophenyl)thio]methylene]-1-naphthyleneacetonitrile;

E-α-[amino[(2-aminophenyl)thio]methylene]-3-(trifluoromethyl)benzeneacetonitrile;

E-α-[amino[(2-aminophenyl)thio]methylene]-1-naphthyleneacetonitrile;

E-α-[amino[(2-aminophenyl)thio]methylene]-2-(trifluoromethyl)benzeneacetonitrile;

E-α-[amino[(4-aminophenyl)thio]methylene]-4-methylbenzeneacetonitrile;

E-α-[amino[(2-aminophenyl)thio]methylene]-2-methylbenzeneacetonitrile;

E-α-[amino[(2-fluorophenyl)thio]methylene]-1-naphthyleneacetonitrile; and,

E-α-[amino[(2-aminophenyl)thio]methylene]-3-phenyl benzeneacetonitrile;

or a pharmaceutically acceptable salt form thereof.

6. A compound according to claim 1, wherein the compound is selected from:

Z-α-[amino[(2-aminophenyl)thio]methylene]-3-[(2,4-dinitrophenyl)hydroxymethyl]benzeneacetonitrile;

Z-α-[amino[(2-aminophenyl)thio]methylene]-3-[(4-carbomethoxyphenyl)hydroxymethyl]benzeneacetonitrile;

Z-α-[amino[(2-aminophenyl)thio]methylene]-3-[(4-nitrophenyl)hydroxymethyl]benzeneacetonitrile;

Z-α-[amino[(2-aminophenyl)thio]methylene]-3-[(pentafluorophenyl)hydroxymethyl]benzeneacetonitrile;

Z-α-[amino[(2-aminophenyl)thio]methylene]-2-methyl-3-[(phenyl)hydroxymethyl]benzeneacetonitrile;

Z-α-[amino[(2-hydroxyphenyl)thio]methylene]-3-[(4-cyanophenyl)hydroxymethyl]benzeneacetonitrile;

Z-α-[amino[(2-aminophenyl)thio]methylene]-3-[(3-nitrophenyl)hydroxymethyl]benzeneacetonitrile;

Z-α-[amino[(2-aminophenyl)thio]methylene]-2-methyl-3-[(pentafluorophenyl)hydroxymethyl]benzeneacetonitrile;

Z-α-[amino[(2-aminophenyl)thio]methylene]-3-[(2-trifluoromethylphenyl)hydroxymethyl]benzeneacetonitrile;

Z-α-[amino[(2-aminophenyl)thio]methylene]-3-[(3-cyanophenyl)hydroxymethyl]benzeneacetonitrile;

Z-α-[amino[(4-aminophenyl)thio]methylene]-3-[(4-cyanophenyl)hydroxymethyl]benzeneacetonitrile;

Z-α-[amino(phenylthio)methylene]-3-[(4-cyanophenyl)hydroxymethyl]benzeneacetonitrile;

Z-α-[amino[(4-aminophenyl)thio]methylene]-2-bromobenzeneacetonitrile;

Z-α-[amino[(2-aminophenyl)thio]methylene]-3-[(2,4-dimethylphenyl)hydroxymethyl]benzeneacetonitrile;

Z-α-[amino[(2-aminophenyl)thio]methylene]-3-[(phenyl)hydroxymethyl]benzeneacetonitrile;

Z-α-[amino[(2-aminophenyl)thio]methylene]-4-chloro-β-phenylbenzepropanenitrile;

Z-α-[amino[(2-thienyl)thio]methylene]-3-[(phenyl)hydroxymethyl]benzeneacetonitrile;

Z-α-[amino[(2,4-diaminophenyl)thio]methylene]-1-naphthyleneacetonitrile;
Z-α-[amino[(4-aminophenyl)thio]methylene]-3-(benzyl)benzeneacetonitrile;
Z-α-[amino[(2-naphthyl)thio]methylene]-1-naphthyleneacetonitrile;
Z-α-[amino[(2-aminophenyl)thio]methylene]-3-(benzoyl)benzeneacetonitrile;
Z-α-[amino[(2-aminophenyl)thio]methylene]-3-phenoxybenzeneacetonitrile;
Z-α-[amino[(2-aminophenyl)thio]methylene]-2-bromobenzeneacetonitrile;
Z-α-[amino[(2-thienyl)thio]methylene]-3-[(2,3,4,5,6-pentafluorophenyl)hydroxymethyl]benzeneacetonitrile;
Z-α-[amino[(4-aminophenyl)thio]methylene]-2-methylbenzeneacetonitrile;
Z-α-[amino[(4-aminophenyl)thio]methylene]-4-(1,1-dimethylethyl)benzeneacetonitrile;
Z-α-[amino[(4-aminophenyl)thio]methylene]-1-naphthyleneacetonitrile;
Z-α-[amino[(2-aminophenyl)thio]methylene]-3-(trifluoromethyl)benzeneacetonitrile;
Z-α-[amino[(2-aminophenyl)thio]methylene]-1-naphthyleneacetonitrile;
Z-α-[amino[(2-aminophenyl)thio]methylene]-2-(trifluoromethyl)benzeneacetonitrile;
Z-α-[amino[(4-aminophenyl)thio]methylene]-4-methylbenzeneacetonitrile;
Z-α-[amino[(2-aminophenyl)thio]methylene]-2-methylbenzeneacetonitrile;
Z-α-[amino[(2-fluorophenyl)thio]methylene]-1-naphthyleneacetonitrile; and,
Z-α-[amino[(2-aminophenyl)thio]methylene]-3-phenyl benzeneacetonitrile;

or a pharmaceutically acceptable salt form thereof.

7. A pharmaceutical composition, comprising: a pharmaceutically acceptable carrier and a therapeutically effective amount of a compound of claim 1 or a pharmaceutically acceptable salt form thereof.

8. A method of treating a condition or disease wherein the disease or condition is referred to as rheumatoid arthritis, osteoarthritis, periodontitis, gingivitis, in a mammal, comprising: administering to the mammal in need of such treatment a therapeutically effective amount of a compound of claim 1 or a pharmaceutically acceptable salt form thereof.

9. A method of treating a condition or disease wherein the disease or condition is referred to as graft versus host reaction in a mammal comprising administering to the mammal in need of such treatment a therapeutically effective amount of a compound of claim 1 or a pharmaceutically acceptable salt form thereof.

10. A pharmaceutical composition, comprising: a pharmaceutically acceptable carrier and a therapeutically effective amount of a compound of claim 3 or a pharmaceutically acceptable salt form thereof.

11. A method of treating a condition or disease wherein the disease or condition is referred to as rheumatoid arthritis, osteoarthritis, periodontitis, gingivitis, in a mammal, comprising: administering to the mammal in need of such treatment a therapeutically effective amount of a compound of claim 3 or a pharmaceutically acceptable salt form thereof.

* * * * *